United States Patent
Sanquer et al.

(10) Patent No.: US 10,731,197 B2
(45) Date of Patent: Aug. 4, 2020

(54) METHODS FOR DETECTING OR QUANTIFYING CTP AND CTP SYNTHASE ACTIVITY

(71) Applicants: Assistance Publique-Hopitaux de Paris, Paris (FR); Imagine Institut Des Maladies Genetiques Necker Enfants Malades, Paris (FR); Universite Paris Descartes, Paris (FR); Institut National de la Sante et de la Recherche Medicale (INSERM), Paris (FR); Centre National de la Recherche Scientifique (CNRS), Paris (FR)

(72) Inventors: Sylvia Sanquer, Sevres (FR); Anne-Claire Boschat, Choisy-le-roi (FR); Sylvain Latour, Vitry sur Seine (FR); Emmanuel Martin, Paris (FR); Robert Barouki, Sevres (FR)

(73) Assignees: Assitance Publique-Hopitaux de Paris (FR); Imagine Institut Des Maladies Genetiques Necker Enfants Malades (FR); Universite Paris Descartes (FR); Institut National de la Sante et de la Recherche Medicale (INSERM) (FR); Centre National de la Recherche Scientifique (CNRS) (FR)

( * ) Notice: Subject to any disclaimer, the term of this patent is extended or adjusted under 35 U.S.C. 154(b) by 190 days.

(21) Appl. No.: 15/767,039

(22) PCT Filed: Oct. 10, 2016

(86) PCT No.: PCT/EP2016/074242
§ 371 (c)(1),
(2) Date: Apr. 9, 2018

(87) PCT Pub. No.: WO2017/060534
PCT Pub. Date: Apr. 13, 2017

(65) Prior Publication Data
US 2018/0298420 A1    Oct. 18, 2018

(30) Foreign Application Priority Data
Oct. 9, 2015  (EP) .................................... 15306609

(51) Int. Cl.
| | | |
|---|---|---|
| C12Q 1/25 | (2006.01) |
| C12Q 1/68 | (2018.01) |
| G01N 33/574 | (2006.01) |
| C12Q 1/6806 | (2018.01) |
| C12Q 1/02 | (2006.01) |
| G01N 30/72 | (2006.01) |
| G01N 30/86 | (2006.01) |
| G01N 30/88 | (2006.01) |

(52) U.S. Cl.
CPC ............... *C12Q 1/25* (2013.01); *C12Q 1/025* (2013.01); *C12Q 1/68* (2013.01); *C12Q 1/6806* (2013.01); *C12Y 603/04002* (2013.01); *G01N 30/7233* (2013.01); *G01N 30/8675* (2013.01); *G01N 33/57484* (2013.01); *G01N 2030/8831* (2013.01); *G01N 2333/9015* (2013.01); *G01N 2500/10* (2013.01)

(58) Field of Classification Search
None
See application file for complete search history.

(56) References Cited

FOREIGN PATENT DOCUMENTS

| | | | |
|---|---|---|---|
| WO | 2006107775 A1 | 10/2006 | |
| WO | 2014170435 A2 | 10/2014 | |
| WO | WO-2014170435 A2 * | 10/2014 | ........... A61K 31/404 |

OTHER PUBLICATIONS

Chen, P. et al., Pharm. Res. 2009, vol. 26, pp. 1504-1515.*
Martin, E. et al, Nature 2014 vol. 510, pp. 288-292.*
Brockman, et al., "The Mechanism of Action of 3-Deazauridine in Tumor Cells Sensitive and Resistant to Arabinosylcytosine", Annals of the New York Academy of Sciences, vol. 255, No. 1, Aug. 1975, pp. 501-521.
Chen, et al., "A LC-MS/MS Method for the Analysis of the Intracellular Nucleoside Triphosphate Levels", Pharmaceutical Research, vol. 26, No. 6, Jun. 2009, pp. 1504-1515.
Cohen, et al., "Liquid Chromatographic Methods for the Determination of Endogenous Nucleotides and Nucleotide Analogs Used in Cancer Therapy: A Review", Journal of Chromatography B, vol. 878, No. 22, Jul. 2010, pp. 1912-1928.
Cohen, et al., "Simultaneous Analysis of Eight Nucleoside Triphosphates in Cell lines by Liquid Chromatography Coupled with Tandem Mass Spectrometry", Journal of Chromatography B, vol. 877, No. 30, Nov. 2009, pp. 3831-3840.

(Continued)

*Primary Examiner* — Heidi Reese
(74) *Attorney, Agent, or Firm* — Lerner, David, Littenberg, Krumholz & Mentlik, LLP

(57) ABSTRACT

The present invention relates to a method for detecting or quantifying CTP in a cell sample comprising at least two nucleotide triphosphates by cationic ion pairing chromatography coupled to mass spectrometry, to a method for detecting or quantifying CTP synthase activity based on the method for detecting or quantifying CTP, and to their use in methods for screening potential immunosuppressive or anti-cancer compounds and in methods for determining the appropriate dose of an immunosuppressive or anti-cancer compound inhibiting CTP synthase activity for a treated subject.

19 Claims, 9 Drawing Sheets

(56) References Cited

OTHER PUBLICATIONS

International Search Report for PCT/EP2016/074242, dated Jan. 27, 2017.

Iyengar, et al., "An Assay for Cytidine 5'-Triphosphate Synthetase Glutaminase Activity Using High Performance Liquid Chromatography", Analytical Biochemistry, vol. 308, No. 2, Sep. 2002, pp. 396-400.

Kuilenburg, et al., "Determination of CTP Synthetase Activity in Crude Cell Homogenates by a Fast and Sensitive Non-Radiochemical Assay Using Anion-Exchange High-Performance Liquid Chromatography", Journal of Chromatography B: Biomedical Sciences and Applications, vol. 693, No. 2, Jun. 1997, pp. 287-295.

Kursula, et al., "Structure of the Synthetase Domain of Human CTP Synthetase, a Target for Anticancer Therapy", Acta Crystallographica Section F: Structural Biology and Crystallization Communications, vol. 62, No. 7, Jul. 2006, pp. 613-617.

Levitzki, et al., "Role of an Allosteric Effector. Guanosine Triphosphate Activation in Cytosine Triphosphate Synthetase", Biochemistry, vol. 11, No. 2, Jan. 1972, pp. 241-246.

Long, et al., "Cytidine Triphosphate Synthetase of *Escherichia coli* B I. Purification and Kinetics", Journal of Biological Chemistry, vol. 242, No. 20, Oct. 1967, pp. 4715-4721.

Magdenoska, et al., "Dispersive Solid Phase Extraction Combined with Ion-Pair Ultra High-Performance Liquid Chromatography Tandem Mass Spectrometry for Quantification of Nucleotides in Lactococcus Lactis", Analytical Biochemistry, vol. 440, No. 2, Sep. 2013, pp. 166-177.

Martin, et al., "CTP Synthase 1 Deficiency in Humans Reveals Its Central Role in Lymphocyte Proliferation", Nature, vol. 510, No. 7504, Jun. 2014, 19 pages.

Wu, et al., "Quantitative Analysis of Intracellular Nucleoside Triphosphates and Other Polar Metabolites Using Ion Pair Reversed-Phase Liquid Chromatography Coupled with Tandem Mass Spectrometry", Journal of Chromatography B, vol. 1006, Dec. 2015, pp. 167-178.

Zhao, et al., "Improved Ruggedness of an Ion-Pairing Liquid Chromatography/Tandem Mass Spectrometry Assay for the Quantitative Analysis of the Triphosphate Metabolite of a Nucleoside Reverse Transcriptase Inhibitor in Peripheral Blood Mononuclear Cells", Rapid Communications in Mass Spectrometry, vol. 27, No. 3, Feb. 2013, pp. 481-488.

* cited by examiner

METHODS FOR DETECTING OR QUANTIFYING CTP AND CTP SYNTHASE ACTIVITY

CROSS REFERENCE TO RELATED APPLICATIONS

The present application is a national phase entry under 35 U.S.C. § 371 of International Application No. PCT/EP2016/074242 filed on Oct. 10, 2016, which claims priority from European Patent Application No. 15306609.7 filed on Oct. 9, 2015, all of which are hereby incorporated herein by reference.

FIELD OF THE INVENTION

The present invention lies in the field of triphosphate nucleotides detection and quantification, and more particularly of CTP synthase activity quantification, for screening or therapy monitoring purposes. More particularly, the present invention relates to a method for detecting or quantifying CTP in a sample comprising triphosphate nucleotides. The present invention also relates to a method for detecting or quantifying CTP synthase activity based on the method for detecting or quantifying CTP. Furthermore, the present invention relates to uses of such methods, and in particular to a method for screening potential of immunosuppressive or anti-cancer compounds and a method for determining the appropriate dose of such compounds.

BACKGROUND OF THE INVENTION

Cytidine is a structural subunit of ribonucleic acid that consists of cytosine and the sugar ribose. Cytidine triphosphate (CTP), an ester of cytidine and triphosphoric acid, is a substance used in the cells to introduce cytidylic acid units into ribonucleic acids. CTP also reacts with nitrogen-containing alcohols to form coenzymes that participate in the formation of phospholipids.
CTP is obtained from uridine triphosphate (UTP) during the pyrimidine biosynthesis. The conversion of UTP into CTP is catalyzed by an enzyme called CTP synthase as follow:

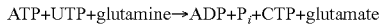

ATP+UTP+glutamine→ADP+$P_i$+CTP+glutamate

CTP synthase, also known under the name of UTP-ammonium ligase, catalyzes the ATP-dependent conversion of UTP in CTP using glutamine or ammonia as a nitrogen source (Long & Arthur. 1967; Kursula et al, 2006). CTP synthase is a polypeptide chain comprising two domains: the C-terminal involved in the hydrolysis of glutamine and in transferring the N-terminal $NH_3$ group used for UTP amination and production of CTP (Weng et al, 1986; Kursula et al, 2006). GTP, in the presence of glutamine, is an allosteric activator of CTP synthase glutaminase activity (Levitzki et al. 1972).

CTP synthase, being a key enzyme involved in nucleic acid and phospholipids synthesis, is involved in cell growth, development, and in tumorigenesis. CTP synthase is also a key enzyme for immune system functionality, insufficiency loss of function of this enzyme leading to immune deficiency. CTP synthase activity inhibitors are already used as anti-cancer compounds but these inhibitors lack specificity. Specific inhibitors of CTP synthase activity might be used as immunosuppressive compounds, particularly to avoid graft rejection after graft transplantation.

In this respect, there is thus a need to detect and quantify CTP and CTP synthase activity.

Different methodologies have been proposed to quantify CTP synthase activity and most are based on the determination of the conversion of UTP into CTP, using either monitoring of changes in absorbance at 291 nm by spectrophotometry (Long et al., 1967), or directly quantifying the nucleotides after chromatographic separation (Van Kuilenburg et al, 1997) or after incorporation of radiolabeled UTP (Brockman et al., 1975). Radioisotope-based methods have the advantage of being very specific, but they are very long, costly and difficult to implement in hospital for routine use. Moreover, the required amount of cells for the implementation of these methods is high, about $10^6$ cells (Cohen et Al.—2010). Methods for quantifying the glutaminase activity of CTP synthase have also been developed (Iyengar et al., 2002). These methods have a high sensitivity but do not provide information on CTP formation.

More recently, it was showed a relationship between deficiency of CTP synthase of type I and the occurrence of severe immune deficiency (Martin et al, 2014), in this study, Martin et al. used a method for quantifying intracellular nucleotides using reversed-phase chromatography coupled to tandem mass spectrometry. However, this method does not allow a good separation of CTP and UTP and is thus not appropriate for determining or quantifying CTP synthase activity. Since all the nucleotides triphosphates have a specific transition, they can be distinguished when using tandem mass spectrometry even when they are not chromatographically separated. However, the inventors have found that there is a 12% interference between UTP and CTP that could be detrimental for CTP dosage when there is an excess of UTP and especially for CTP synthase activity assays since the samples are incubated with a large excess of UTP.

Moreover, most prior art methods for detecting and quantifying CTP and CTP synthase activity are time consuming, i.e the duration of nucleotides separation (separation time) takes more than 15 minutes and the total duration of analysis (run time) takes often more than 40 minutes (Cohen et al, 2009, Ping et al., 2009, WO 2006/107775).

An additional problem of some of these methods (for example those described by Cohen et al., 2009) is that, during the cell extracts preparation, CTP synthase is denatured and it is thus not possible to further measure accurately its enzymatic activity.

More generally, it appears that current methods for detecting and quantifying CTP and CTP synthase activity are time consuming, costly, require samples with high cell numbers, conduct to proteins denaturation, and thus do not allow specific detecting or quantifying of CTP or CTP synthase activity.

Thus, there is a need to provide alternative methods for detecting or quantifying CTP or CTP synthase activity, which overcomes the drawbacks of prior art methods.

Particularly, it is necessary to provide a method allowing an optimal separation between CTP and other nucleotides in the sample (in particular UTP), having a high specificity, without proteins denaturation at the stage of cellular extracts preparation, being less time consuming and requiring lower cell numbers in cell sample compared to prior art methods, and having good intravariability and intervariability. It is also necessary that this method be appropriate to routine hospital implementation.

SUMMARY OF THE INVENTION

In the context of the present invention, the inventors have now found that cationic ion pairing chromatography coupled to mass spectrometry allows detecting and quantifying CTP and/or CTP synthase activity in short time, with high specificity, without proteins denaturation at the stage of cellular extracts preparation, intravariability and intervariability, in cell samples containing low numbers of cells.

While liquid chromatography coupled to mass spectrometry has been used in the art for detection and/or quantification of various compounds, there are many types of liquid chromatography known in the art that may be coupled to mass spectrometry, many of which could a priori be used for the detection or the quantification of CTP and CTP synthase activity and it is difficult and time consuming to adapt and combine these technics in order to obtain an optimal method for detecting or quantifying CTP or CTP synthase activity allowing overcoming the above-mentioned drawbacks. The inventors have tested several types of possible liquid chromatography (different types of columns and different mobile phases), and found that many combinations do not permit to detect or quantify CTP or CTP synthase activity rapidly, without proteins denaturation at the stage of cellular extracts preparation, with high intravariability and intervariability, and thus do not overcome the drawbacks of prior art methods (see Comparative Example). Ion pairing chromatography is generally not used coupled to mass spectrometry, because ion pair reagents are known to lead to fouling of mass spectrometer ion source and deteriorate the LC column performance (Zhao et al, 2013). Ion pairing chromatography is thus generally not recommended by mass spectrometer manufacturers. However, the inventors surprisingly found that cationic ion pairing chromatography, in particular performed with a sample having acid pH, coupled to mass spectrometry was the only tested liquid chromatography-mass spectrometry (LC-MS) technology actually permitting rapid detection and quantification of CTP and CTP synthase activity, with high intravariability and intervariability.

In a first aspect, the present invention thus relates to a method for detecting or quantifying CTP in a sample comprising at least two distinct triphosphate nucleotides, said method comprising:
  a) separating the distinct triphosphate nucleotides by ion pairing chromatography using a cationic ion pair reagent contained in a mobile phase having pH comprised between 6 and 7, wherein the sample injected for the chromatography has a pH comprised between 1 and 7 and
  b) detecting or quantifying CTP by mass spectrometry.

The inventors have demonstrated that the use of ion pairing chromatography using a cationic pair reagent, preferably in a mobile phase having a pH comprised between 6 and 7 and preferably using an acid sample allows separating CTP of the other triphosphate nucleotides in a cell sample very quickly and with high accuracy, better storage of samples, better signal quality, thus permitting specific CTP detection and quantification by coupled mass spectrometry.

Obviously, it is essential to accurately separate CTP from other triphosphate nucleotides (and in particular from UTP) in order to detect or quantify CTP synthase activity, since CTP synthase activity detection or quantification relies on the measurement of transformation of UTP into CTP by CTP synthase. Moreover, as indicated above, the method of the invention is characterized by high signal quality due to better source ionization and better sample storage in the sample changer.

In a second aspect, the present invention thus relates to a method for detecting or quantifying CTP synthase activity in a cell sample, said method comprising:

a) optionally, stimulating said cell sample with a lymphocyte activating molecule, such as PMA/ionomycine,
  b) preparing a cell extract by lysing cells of said cell sample,
  c) incubating the cell extract prepared in step b) in the presence of UTP, ATP, GTP and glutamine in conditions suitable for CTP synthase activity; and
  d) detecting or quantifying CTP generated by CTP synthase comprised in the cell extract using the method of detecting or quantifying CTP according to the invention.

In step b), in order to avoid denaturation of CTP synthase, the cell extract is preferably collected in a neutral to basic buffer, preferably a buffer of pH between 7 and 9, preferably between 7.5 and 8.5, for instance about 8.0. Similarly, step c) is preferably performed in a buffer of pH between 7 and 9, preferably between 7.5 and 8.5, for instance about 8.0, during 90-min enzymatic conversion of UTP to CTP. The enzymatic reaction may then be stopped by acidifying the sample to an acid pH, preferably between 3 and 4 Indeed, a neutral to basic intermediate pH is optimal for CTP synthase activity and an acidic buffer, as required for stable conservation and analysis of nucleotides, is known to precipitate proteins and therefore the enzymatic activity of CTP synthase would be lost (steps b and c). In this respect, the method of the invention thus permits accurate for detection or quantification of CTP synthase activity.

In step c) of the method for detecting or quantifying CTP synthase activity, the cell extract may be also incubated in the presence of phosphoenolpyruvate (PEP) and sodium fluoride (NaF) which may be add to UTP, ATP, GTP and glutamine. This is because when PEP and NaF are added to UTP, ATP, GTP and glutamine during the step of incubation, they allow ATP regeneration during the enzymatic reaction. NaF is used to maintain protein phosphorylation status of the cell extract and PEP favors ATP regeneration during the enzymatic reaction, the main energy source of CTP synthase.

Compounds inhibiting CTP synthase activity are used as anti-cancer agents for treating subject in need thereof and may also be used as immunosuppressive agents.

Since the method of the present invention allows specifically detecting or quantifying CTP synthase activity, it may thus be used for screening immunosuppressive and/or anti-cancer compounds.

In a third aspect, the present application thus relates to a method for screening potential immunosuppressive or anti-cancer compounds, said method comprising:
  a) quantifying CTP synthase activity in an untreated cell sample and in a cell sample treated with a test compound using the method for detecting or quantifying CTP synthase activity according to the invention,
  b) selecting the test compound as an immunosuppressive or anti-cancer compound if the CTP synthase activity quantified in step a) is lower in the treated cellular sample than in the untreated cellular sample.

The methods of the present application allow detecting or quantifying CTP and CTP synthase activity with very high accuracy in a short time (less than 15 min), without protein and thus CTP synthase denaturation at the stage of cellular extracts preparation, based on a small number of cells, and using technologies that may be easily implemented in a hospital setting. These methods could thus be used particularly to evaluate an immunosuppressive or an anti-cancer treatment efficacy in a treated subject and if necessary adapting and optimizing the treatment dose.

In a forth aspect, the present application thus relates to a method for determining the appropriate dose of an immunosuppressive or anti-cancer compound inhibiting CTP synthase activity for a treated subject, said method comprising:
 a) quantifying CTP synthase activity using the method for detecting and quantifying the CTP synthase activity according to the invention in a cell sample from said subject treated with an immunosuppressive or anti-cancer compound,
 b) optimizing the dose of immunosuppressive or anti-cancer compound according to the quantified CTP synthase activity.

More generally, the present invention also relates to the use of the method for detecting or quantifying CTP according to the invention for:
 detecting or quantifying CTP synthase activity,
 screening immunosuppressive or anti-cancer compounds, and/or
 adapting the dose of immunosuppressive or anti-cancer compound inhibiting CTP synthase activity for a treated subject.

The present invention also relates to the method for detecting or quantifying CTP synthase activity according to the invention for:
 screening immunosuppressive or anti-cancer compounds, and/or
 adapting the dose of immunosuppressive or anti-cancer compounds inhibiting CTP synthase activity for a treated subject.

DETAILED DESCRIPTION OF THE INVENTION

Definitions

Figure 1:
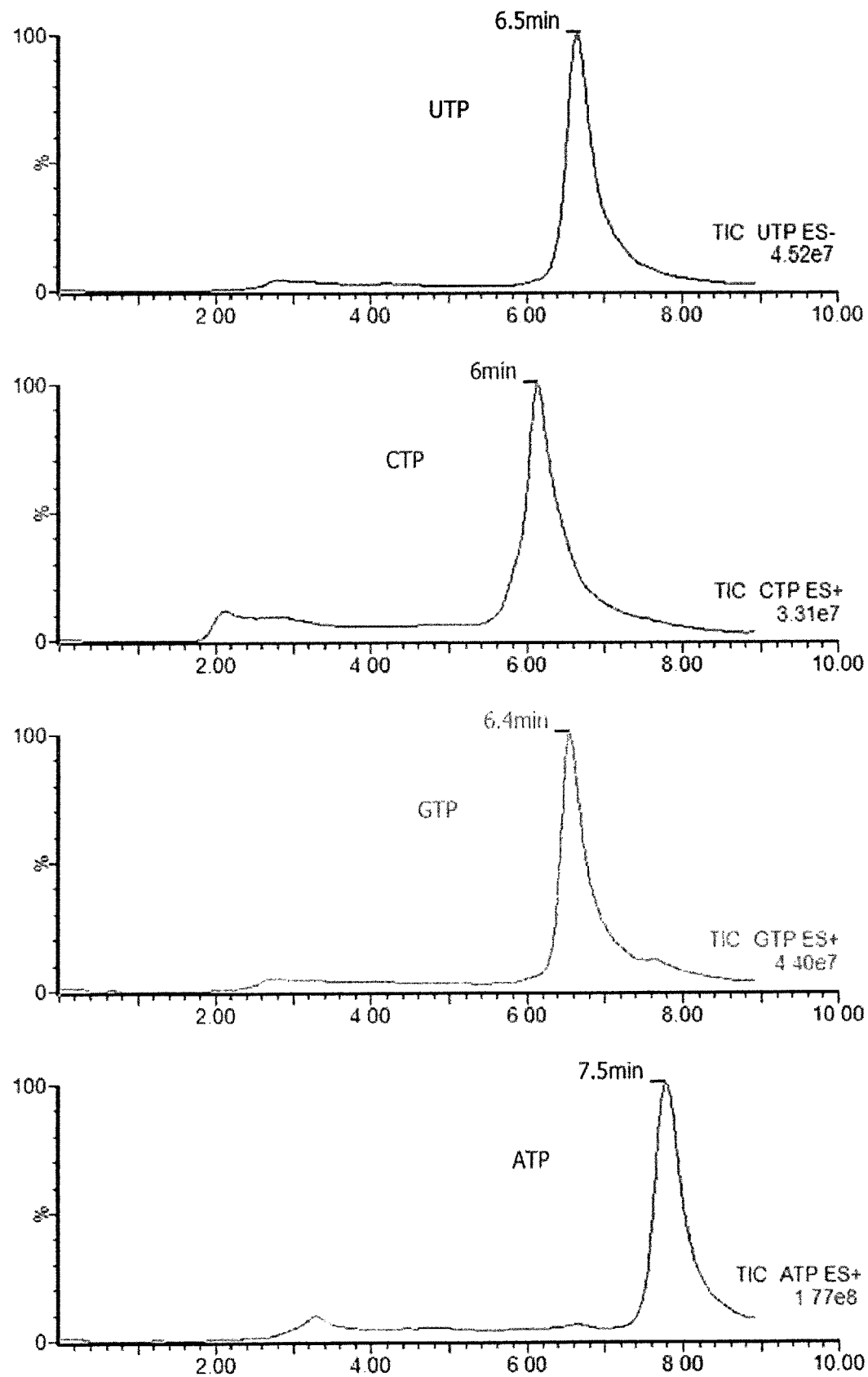
FIG. 1: Linear time gradient of separation (12 min) of four triphosphate nucleotides UTP, CTP, GTP and ATP detected by using HSS T3 column in presence of ACN and dibutylamine acetate (DBA which is a cationic ion pair reagent).

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

In the present application, the term "CTP" or "cytidin triphosphate" (see formula below) refers to a pyrimidine nucleoside triphosphate, which is a substrate in the synthesis of RNA. CTP is a coenzyme in metabolic reactions like the synthesis of glycerophospholipids and glycosylation of proteins. CTP acts as an inhibitor of the enzyme aspartate carbamoyltransferase, which is used in pyrimidine biosynthesis.

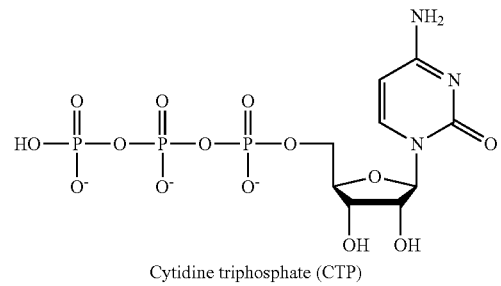
Cytidine triphosphate (CTP)

In the present application, the term "UTP" or "uridine triphosphate" refers to a pyrimidine nucleoside triphosphate, consisting of the organic base uracil linked to the 1' carbon of the ribose sugar, and esterified with tri-phosphoric acid at the 5' position. It is a substrate for the synthesis of RNA during transcription.

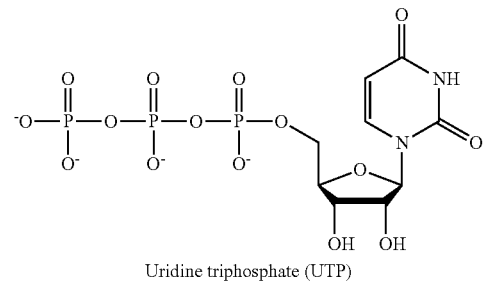
Uridine triphosphate (UTP)

In the present invention, the term "CTP synthase" or "CTP synthetase" refers to an enzyme involved in pyrimidine biosynthesis that interconverts UTP and CTP. The reaction proceeds by the ATP-dependent phosphorylation of UTP on the 4-oxygen atom, making the 4-carbon electrophilic and vulnerable to reaction with ammonia. The source of the amino group in CTP is glutamine, which is hydrolysed in a glutamine amidotransferase domain to produce ammonia. This is then channeled through the interior of the enzyme to the synthetase domain. Here, ammonia reacts with the intermediate 4-phosphoryl UTP, as represented below:

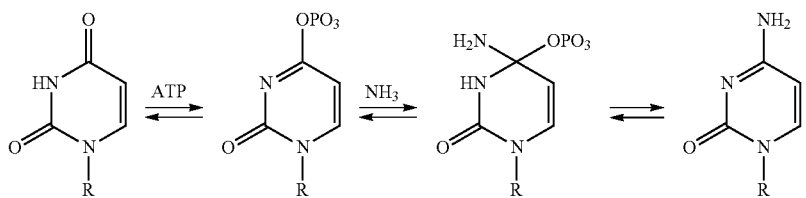

Conversion of UTP into CTP by CTP synthase (R = ribose triphosphate)

In the present application, the term "reverse phase chromatography" or RPC refers to any chromatographic method that uses a hydrophobic stationary phase and a polar (aqueous) mobile phase. As a result, hydrophobic molecules in the polar mobile phase tend to adsorb to the hydrophobic stationary phase, and hydrophilic molecules in the mobile phase will pass through the column and are eluted first. Hydrophobic molecules can be eluted from the column by decreasing the polarity of the mobile phase using an organic solvent, which reduces hydrophobic interactions. The more hydrophobic is the molecule, the more strongly it will bind to the stationary phase, and the higher concentration of organic solvent that will be required to elute the molecule. RPC refers to liquid (rather than gas) chromatography.

In the present invention, the terms "stationary phase" or "column" refer to a solid substance fixed in place for the chromatography procedure, which acts as a constraint on many of the components of the analyzed sample, slowing them down to move slower than the mobile phase. In liquid chromatography, the stationary phase is generally a column comprising particles with bead shape.

In the present invention, the term "mobile phase" refers to a liquid or gaseous (preferably liquid) substance that moves in a definite direction. The mobile phase comprises the components of the sample being separated/analyzed in aqueous and/or organic solvents and carries the components of the sample being separated/analyzed through the stationary phase. The movement of the components in the mobile phase is controlled by the significance of their interactions with the mobile and/or stationary phases. Because of the differences in factors such as the solubility of certain components in the mobile phase and the strength of their affinities for the stationary phase, some components will move faster than others, thus facilitating the separation of the components within the sample.

In the present invention, the term "retention time" refers to the time required for a particular analyte to pass through the system (from the column inlet to the detector) under particular conditions.

In the present invention, the expression "separation time" refers to the time necessary to separate CTP from the other nucleotides, particularly from UTP. Typically, in the method for detecting and quantifying CTP according to the invention, the separation time corresponds to the time necessary to perform chromatographic step a) of the method.

In the present invention, the expression "analysis time" or "run time" relates to the time necessary to perform the whole method of the invention for determining and quantifying the CTP (i.e. at least steps a) and b)).

In the present invention, the term "gradient time" refers to the time over which the solvent composition is changed.

In the present invention, the term "intravariability" refers to variation in repeat measurements made on the same sample under identical conditions. Intravariability is generally tested by performing the same chromatography in the same conditions (same sample, same chromatographic conditions, over a short period of time) 10 times in the same day, and measuring variations of the 10 measurements.

In the present invention, the term "intervariability" refers to variation in measurements made on a sample under changing conditions. In the context of the present invention, intervariability mainly refers to variation in measurements made on a sample under an extended period of time, and may notably be measured by performing the same chromatography in the same conditions each day during 10 separate days.

In the present application, the term "ion pairing chromatography" or "IPC" refers to a technology used to separate charged substances using ion-pairing reagents as mobile phase additives, preferably allowing the separation of ionic and highly polar substances on reverse phase chromatography stationary phases.

In the present application, the term "ion pair reagent" refers an ionic compound which is added to the mobile phase and which is capable to promote the formation of an ion pair with a charged analyte.

In the present invention, the term "cationic ion pair reagent" refers to an ionic compound having a positively charged ion which is capable to promote formation of an ion pair with a negatively charged analyte.

In the present invention the term "mass spectrometry" or "MS" refers to an analytical chemistry technique that helps identify the amount and type of chemicals present in a sample by measuring the mass-to-charge ratio (m/z ratio) and abundance of gas-phase ions.

In the present invention, the term "electrospray ionization" or "ESI" refers to a technique used in mass spectrometry to produce ions using an electrospray, in which a high voltage is applied to a liquid to create an aerosol. Mass spectrometry using ESI is called electrospray ionization mass spectrometry (ESI-MS) or electrospray mass spectrometry (ES-MS).

In the present invention, the term "tandem mass spectrometry" or MS/MS refers to any general method involving at least two stages of mass analysis, either in conjunction with a dissociation process or in a chemical reaction that causes a change in the mass or charge of an ion.

In the present invention, the term "anti-cancer compound" refers to any compound which is capable to kill, inhibit the growth or invasiveness of cancer cells. Anticancer compounds notably include CTP synthase inhibitors, which are compounds that inhibit CTP synthase activity. Examples of CTP synthase inhibitors include 3-deazauridine, acivicin, cyclopentenyl cytosine, DON (6-diazo-5-oxo-L-nor-leucine) and G1 compound.

In the present invention, the term "immunosuppressive compound" refers to any compound capable to reduce or prevent immune responses Immunosuppressive compounds also include CTP synthase inhibitors, since loss of function of CTP synthase is known to lead to immune deficiency.

Method for Detecting or Quantifying CTP in a Sample Comprising at Least Two Distinct Nucleotides.

In the context of the present invention, the inventors have found that combining a reverse phase chromatography stationary phase using a specific solid substrate with the use of a mobile phase comprising a cationic ion pair reagent (preferably when the pH of the mobile phase is acid, in particular comprised between 6 and 7, and the pH of the sample injected is acid too) allows obtaining a very good separation between the different nucleotide triphosphates contained in a sample, contrary to many other liquid chromatography-mass spectrometry technologies.

This finding is very important since it allows detecting or quantifying CTP with high precision very quickly, which will be useful every time one needs to detect or quantify said nucleotide precisely, particularly for medical use for screening compounds or adjusting the dose of therapeutic compounds.

In a first aspect, the present invention thus relates to a method for detecting or quantifying CTP in a sample comprising at least two distinct nucleotide triphosphates, said method comprising:
  a) separating the distinct nucleotide triphosphates by ion pairing chromatography using a cationic ion pair reagent contained in a mobile phase having pH comprised between 6 and 7, wherein the sample injected for the chromatography has a pH comprised between 1 and 7, and
  b) detecting or quantifying CTP by mass spectrometry.

Liquid chromatography is a classical tool in chemistry and biology to detect or quantify compounds of interest. However, many types of chromatography may a priori be used. Usually, in order to separate CTP, an anion-exchange chromatography is used, which is a process that separates substances based on their charges using an ion-exchange resin containing positively charged groups, such as diethylaminoethyl groups (DEAE). In solution, the resin is coated with positively charged counter-ions (cations). Anion exchange resins will bind to negatively charged molecules and displace the counter-ion.

Reverse phase chromatography may also be used for separating CTP. The inventors have tested several types of reverse phase chromatography columns but found that separation of CTP from other nucleotide triphosphates (and in particular from UTP) was not sufficient to permit CTP synthase activity detection or quantification.

Then, the inventors decided to introduce high concentrations of ion-pairing reagents into the mobile phase to separate CTP from the others nucleotide triphophates contained in the sample such as uridine triphosphate (UTP), adenosine triphosphate (ATP) or guanosine triphosphate (GTP), and found that combination of a reverse phase chromatography column and of a mobile phase containing a cationic ion pair reagent surprisingly permitted sufficient, repeatable and reproducible separation of CTP from other nucleotide triphophates and in particular from UTP. The mobile phase containing ion pair reagents preferably has an acid pH, in particular comprised between 6 and 7, preferably between 6.3 and 6.7, more preferably the mobile phase has a pH of 6.5. The analyzed sample injected on the chromatography column in steps a) preferably also has an acid pH, in particular comprised between 1 and 7 or 1 and 6, preferably between 3 and 7 or 3 and 6 and more preferably between 3 and 4. The method of the invention is particularly advantageous since it is not necessary to neutralize the pH of the sample to be analyzed, which may be deposited directly (with acid pH) on the chromatography column. This allows saving time of neutralization of the sample and thus performing the method of detection and quantification of CTP very quickly compared to prior art methods.

Analyzed Sample

The sample to be analyzed comprises at least two distinct nucleotide triphosphates, one of which is preferably CTP. It thus also comprises at least one of UTP, ATP and GTP. Preferably, it comprises CTP and UTP, and may further comprise ATP and/or GTP.

According to a preferred embodiment of the present invention, the analyzed sample is a blood sample, preferably a PBMC sample and more preferably a lymphocyte sample. Said sample may be isolated directly from human blood or from previously prepared cell culture.

Before step a) of separating the distinct nucleotide triphosphates by ion-pairing chromatography using a cationic ion pair reagent, the method may of course include any step necessary to prepare the sample for such separation.

In particular, when the method involves directly detecting or quantifying CTP from a cellular extract comprising at least two distinct nucleotides starting from a blood, PBMC or lymphocyte sample, cells are preferably lyzed using any appropriate technology in order to liberate the cell content, and cellular debris are preferably removed in order to obtain a cellular extract comprising the at least two nucleotide triphosphates. Preferably, the cellular extract is collected at an acid pH, preferably between 2 and 3 in order to preserve nucleotide triphosphates and in particular CTP.

However, in the context of CTP synthase activity detection or quantification, while the nucleotide triphosphates sample obtained after enzymatic reaction of a cellular extract with CTP synthase is preferably put at an acidic pH, preferably between 3 and 4 at the end of the enzymatic reaction, the cellular extract is first preferably collected at a neutral to basic intermediate pH between 7 and 9, preferably between 7.5 and 8.5, for instance about 8.0, in order to avoid CTP synthase denaturation until the enzymatic reaction time leading to CTP formation from UTP.

Step a): Cationic Ion Pairing Chromatography Step a)

Stationary Phase

Preferably, the stationary phase used in the present invention is adapted to retain compounds having strong polarity such as nucleotide triphosphates.

According to a preferred embodiment of the method of the invention, step a) is performed by using a reverse phase column, preferably comprising beads of a diameter inferior or equal to 10 µm grafted with a hydrophobic molecule.

According to one embodiment, the beads diameter is comprised between 1 and 10 µm, between 1 and 5 µm, preferably, between 1 and 3 µm and more preferable between 1 and 2 µm.

Alternatively or in combination, beads may be made of any appropriate material, including silica (and notably High Strength Silica (HSS)), Ethylene Bridged Hybrid (BEH), Charged Surface Hybrid (CHS), and Charged Surface Hybrid (CSH). In a preferred embodiment, step a) is performed by using a reverse phase column comprising beads of high strength silica with a diameter comprised between 1 and 10 μm.

Alternatively or in combination, the beads in the column of the present invention may be porous and pore size is preferably comprised between 50 and 350 Å, preferably between 100 and 300 Å, more preferably between 100 and 200 Å and even more preferably between 100 and 130 Å. According to the preferred embodiment of the present invention the pore size is 100 Å. In a preferred embodiment, step a) is performed by using a reverse phase column comprising beads of high strength silica with a diameter comprised between 1 and 10 μm and a pore size between 100 and 130 Å.

Alternatively or in combination, the hydrophobic molecule grafted to the column (preferably to the beads) as used in the present invention is selected from linear, branched or cyclic, saturated or unsaturated, hydrocarbon chains compounds. Preferably, the hydrocarbon chain comprises 6 to 30 carbon atoms, more preferably 8 to 27 carbon atoms, 12 to 21 carbon atoms and even more preferably 18 to 21 carbon atoms, and in particular 18 carbon atoms. In a preferred embodiment, the hydrocarbon chain is selected from $C_6$-$C_{30}$ (preferably $C_8$-$C_{21}$, $C_{12}$-$C_{21}$, more preferably $C_{18}$-$C_{21}$, or even $C_{18}$) linear or branched (preferably linear) alkyls and $C_6$-$C_{30}$ aryl or arylalkyl groups (such as $C_6$ alkyl-phenyl or propyl fluorophenyl). In a particularly preferred embodiment, the hydrocarbon chain is a linear $C_{18}$ alkyl.

Table 1 below shows examples of columns that may be used in the present invention.

TABLE 1

Examples of columns that may be used in the invention

| Columns | Ethylene Bridged Hybrid BEH 300 C18 | High Strength Silica HSS T3 | Charged Surface Hybrid CSH Fluoro-Phenyl | Charged Surface Hybrid CSH Phenyl-Hexyl |
| --- | --- | --- | --- | --- |
| Particles/Size | Ethylene Bridged Hybrid 1.7 μm | High Strength Silica 1.8 μm | Charged Surface Hybrid 3.5 μm | Charged Surface Hybrid 1.7 μm |
| Grafted with | C18 | T3(C18) | Propyl Fluorophenyl | $C_6$Phenyl |
| Pores size | 300 Å | 100 Å | 130 Å | 130 Å |
| Type | Reverse phase | Reverse phase | Reverse phase | Reverse phase |
| Diameter/Length | 2.1 mm/100 mm | 2.1 mm/100 mm | 2.1 mm/100 mm | 2.1 mm/100 mm |

According to particularly preferred embodiments of the invention, the column used in step a) is:
- a reverse phase column comprising High Strength Silica (HSS) beads with a diameter comprised between 1 and 10 μm, grafted with a linear C18 alkyl
- a reverse phase column comprising High Strength Silica (HSS) beads with a diameter comprised between 1 and 10 μm, a pore size of 100 to 130 Å (preferably 100 Å), grafted with a linear C18 alkyl; more preferably the column used in step a) is a High Strength Silica T3 C18 (also called HSS T3 C18). Such column may be purchased from Waters under the name UPLC Acquity™.

Mobile Phase

According to a preferred embodiment of the invention, the mobile phase containing the cationic ion pair reagent is based on water and on a varying amount of a water-miscible organic modifier (gradient of water-miscible organic modifier in an aqueous solution comprising the ion pairing reagent).

The organic modifier is preferably selected from acetonitrile (ACN), methanol, ethanol and isopropanol, more preferably the organic modifier is acetonitrile.

The mobile phase is obtained by forming a binary gradient (preferably linear) of an aqueous solution A comprising water and the cationic ion pair reagent and of an organic solution B comprising the organic modifier and the cationic ion pair reagent.

Preferably the mobile phase contains water, the cationic ion pair reagent, and a varying amount of acetonitrile, obtained by forming a binary gradient (preferably linear) of an aqueous solution A comprising water and the cationic ion pair reagent and of an organic solution B comprising acetonitrile and the cationic ion pair reagent. Columns (stationary phase) suitable for use in the present invention are well known to skilled artisans, who will easily adapt the detailed parameters of the mobile phase depending on the specific column used.

However, in order to perform the method of present invention and obtain a good separation of CTP from the other nucleotide triphosphates present in the sample, it is necessary to introduce in the mobile phase a cationic ion pair reagent.

According to a preferred embodiment of the present invention, the cationic ion pair reagent is selected from quaternary ammonium salts, in particular from salts (in particular acetate salts) of di-, tri-, or tetra-($C_1$-$C_4$ alkyl)-amine. More preferably, the cationic ion pair reagent is dibutylamine acetate or tributylamine acetate, most preferably dibutylamine acetate (DBA).

The cationic ion pair reagent is preferably present in the mobile phase in a concentration comprised between 5 and 10 mM, preferably between 5 and 8 mM and more preferably, between 5 and 6 mM.

In particularly preferred embodiment of the invention, the mobile phase is obtained by forming a binary gradient (preferably linear) of an aqueous solution A comprising water and dibutylamine acetate in a concentration of 5-10 mM and of an organic solution B comprising acetonitrile and dibutylamine acetate in the same concentration of 5-10 mM.

Furthermore, the inventors have found that with the method of the invention it is advantageous to control the mobile phase pH. According to one embodiment, the mobile phase have a pH comprised between 6 and 7, preferably between 6.3 and 6.7, more preferably the mobile phase have a pH of 6.5. In particular, the mobile do not comprise acetic acid.

Preferred Combinations of Stationary and Mobile Phases

In the context of the invention, each list of appropriate features for a particular element and each specific feature disclosed for a particular element may be combined with any generic other element, list of appropriate features for said other element or any specific feature disclosed for said other element.

In particular, preferred embodiments of an element (such as the type of stationary phase and/or the composition of the mobile phase) of the method for detecting or quantifying CTP or CTP synthase activity according to the invention may be combined with any generic other element or with preferred embodiments of said other element.

Preferred combinations of stationary and mobile phases are listed in Table 2 below.

TABLE 2

Preferred combinations of stationary and mobile phases

| Stationary phase | | | | Mobile phase | | |
|---|---|---|---|---|---|---|
| bead material | bead diameter | grafted molecule | pore size | organic modifier | cationic ion pair reagent | cationic ion pair reagent concentration |
| silica | 1-10 µm | linear C12-C21 alkyl | | acetonitrile | di-, tri-, or tetra-(C1-C4 alkyl)-amine salt | 5-10 mM |
| silica | 1-10 µm | linear C12-C21 alkyl | 50-350 Å | acetonitrile | di-, tri-, or tetra-(C1-C4 alkyl)-amine salt | 5-10 mM |
| high strength silica | 1-5 µm | linear C18 alkyl | | acetonitrile | dibutylamine acetate or tributylamine acetate | 5-6 mM |
| high strength silica | 1-5 µm | linear C18 alkyl | 100-130 Å | acetonitrile | dibutylamine acetate or tributylamine acetate | 5-6 mM |

Chromatographic Parameters pH:

Classically, in liquid chromatography, the pH of sample injected onto the column has to be about 7 in order to permit accurate separation and to maintain the performance of the column Consequently, in case of an acidic sample (as it is the case for nucleotide triphosphates), it is generally recommended to add a step of neutralizing the sample before injection onto the chromatographic column.

The inventors have unexpectedly found that with the method of the invention the sample may be injected onto the column at acidic pH (pH<7), without altering the separation efficiency of nucleotide triphosphates.

Thus, according to one embodiment, the sample is injected at pH lower than 7. Preferably, the pH of the sample injected onto the column is comprised between 1 and 7 or between 1 and 6, preferably between 3 and 7 or between 3 and 6 and more preferably between 3 and 4. As mentioned above, the method of the invention is particularly advantageous since even when the pH of the sample is acid it is possible to separate CTP from other nucleotides without damaging the chromatography column. Using acid sample also allows their storage in sample changer and better separation since the signal quality is high.

As indicated above, the method of the invention is particularly advantageous since it is not necessary to neutralize the pH of the sample to be analyzed before injection, which may be deposited directly (with acid pH) on the chromatography column. This allows saving time of neutralization of the sample and thus performing the method of detection and quantification of CTP very quickly compared to prior art methods.

Duration of Chromatographic Separation:

Advantageously, the method for detecting or quantifying CTP in a sample containing at least two nucleotide triphosphates according to the invention allows an efficient and rapid separation between CTP and the other nucleotide triphosphates. Thus, as illustrated in the examples, a separation time (i.e. a duration of step a)) of at most 20 minutes, preferably at most 15 minutes, more preferably at most 12 minutes, at most 10 minutes, at most 9 minutes, at most 8 minutes, at most 7 minutes or even about 6 minutes is preferred.

Currently, separation time of CTP in some methods of the prior art is higher than 18 min (Cohen et al., 2009 and Ping et al., 2009).

The short separation time in the method of the invention may be obtained by forming a binary gradient (preferably linear) of an aqueous solution A comprising water and the cationic ion pair reagent (preferably dibutylamine acetate or tributylamine acetate, more preferably dibutylamine acetate) and of an organic solution B comprising the organic modifier (preferably acetonitrile) and the cationic ion pair reagent (preferably dibutylamine acetate or tributylamine acetate, more preferably dibutylamine acetate), the ratio volume/volume (v/v) of solution A to solution B varying from 95/5 to 85/15 at t=0 minute to 95/5 to 50/50 at t=5 to 15 minutes. A preferred example of suitable gradient is:

89/11 at t=0 minute to 88/12 at t=6 minutes

The programmed mobile-phase gradient that is used during a 9-min run (analysis or run time) is as follows: 0 min, 11% B; 8 min, 13% B; 8.1 min, 100% B; 8.5 min, 100% B; 8.6 min, 11% B; 12 min, 11% B.

The times of retention onto the column of the distinct nucleotide triphosphates (in particular of CTP and UTP) should be sufficiently different to allow their efficient separation. In particular, the times of retention onto the column of the distinct nucleotide triphosphates (in particular of CTP and UTP) should preferably differ of at least 0.25 minutes (i.e. at least 15 seconds), preferably at least 0.3 minutes (i.e. at least 18 seconds), at least 0.35 minutes (i.e. at least 21 seconds), at least 0.4 minutes (i.e. at least 24 seconds).

Preferably the separation is obtained by forming a binary gradient of an aqueous solution A and of an organic solution B as defined above, which is a quasi-isocratic gradient. Hence, from the beginning (t=0) to the end of the separation step, there is preferably an increase of the % (v/v) of the organic solution B of at most 10% (v/v) (e.g. from 10% (v/v) at t=0 to 20% (v/v) at the end of the separation step), more preferably at most 5% (e.g. from 10% (v/v) at t=0 to 15% (v/v) at the end of the separation step), even more preferably at most 2% (v/v) (e.g. from 10% (v/v) at t=0 to 12% (v/v) at the end of the separation step).

Step b): Mass Spectrometry

After step a) of separation of CTP from the other nucleotide triphosphates in the sample, CTP is detected or quantified using mass spectrometry (MS).

According to a preferred embodiment, CTP is detected and/or quantified using electrospray ionization mass spectrometry.

Alternatively or in combination, tandem mass spectrometry is also used.

In a particularly preferred embodiment, CTP is detected and/or quantified using electrospray ionization tandem mass spectrometry.

For quantification, two transitions are preferably analyzed for each nucleotide triphosphate, in order to improve method precision.

Transitions that may be used when using electrospray ionization tandem mass spectrometry are presented in Table 3 below.

TABLE 3

Transitions parameters for UTP, ATP, GTP, CTP, and CTP-EI (stable isotope CTP standard)

| Nucleotide triphosphate | Quantification transition | Collision energy | Confirmation transition | Collision energy |
|---|---|---|---|---|
| UTP | 482 > 158.9 | 28 | 482 > 384.9 | 20 |
| ATP | 507.9 > 136 | 32 | 507.9 > 507.9 | 2 |
| GTP | 523.9 > 152 | 24 | 523.9 > 523.9 | 2 |
| CTP | 484 > 112 | 20 | 484 > 484 | 2 |
| CTP-EI | 495.8 > 119 | 26 | / | / |

Stable Isotope CTP Standard

In a preferred embodiment of the method of quantifying CTP according to the invention, a stable isotope CTP standard is added to the sample before step a) of the method.

This standard is used to precisely quantify the amount of CTP present in the sample.

The stable isotope CTP standard is such that its transition parameters are different from normal CTP present in the sample, so that the stable isotope CTP standard may be distinguished from the normal CTP present in the sample (see Table 3 above).

Such a stable isotope CTP standard may be obtained from Sigma-Aldrich under the name Cytidine-$^{13}$C9, $^{15}$N3 5'-triphosphate sodium salt.

Analysis Time (or Run Time)

According to the method of the present invention, the analysis time is very short, preferably said analysis time is of at most 20 min, more preferably of at most 15 min and even more preferably of at most 12 min. This is very advantageous since it is much more rapid than the analysis time of other prior art methods For example, the analysis time of the method described by Cohen et al (2009) is 40 min ((see Materials and Methods and FIG. 3) and those of the method described by Ping et al. (2009) is 68 min (see Materials and Methods and FIG. 1).

Method for Detecting or Quantifying CTP Synthase Activity in Cell Sample

In order to detect or quantify CTP synthase activity accurately, it is necessary to efficiently separate CTP and UTP, since the formation of CTP from UTP by CTP synthase is to be quantified. It is also necessary that the separation of these nucleotides does not induce CTP synthase denaturation and thus decreasing the accuracy of CTP synthase activity detection or quantification.

In a second aspect, the present invention thus relates to a method for detecting or quantifying CTP synthase activity in a cell sample, said method comprising:

a) optionally, stimulating said cell sample with a lymphocyte activating molecule such as PMA/ionomycine,
b) preparing a cell extract by lysing cells of said cell sample,
c) incubating the cell extract prepared in step b) in the presence of UTP, ATP, GTP and glutamine in conditions suitable for CTP synthase activity; and
d) detecting or quantifying CTP generated by CTP synthase comprised in the cell extract using the method for detecting or quantifying CTP according to the invention.

Cell Sample

Generally, conventional radio-isotopic methods require at least $10^6$ cells for the detection or the quantification of CTP synthase activity.

Advantageously, due to its high sensitivity, the method of the invention requires only at least $10^5$ cells for efficiently detecting or quantifying of CTP synthase activity.

It is particularly advantageous when the cell sample is a lymphocyte cell sample and when the CTP synthase activity is quantified in a subject with CTPS1 deficiency or treated with immunosuppressive compounds (and thus with low CTP synthase activity).

Optional Step a)

According to an embodiment of the method for detecting or quantifying CTP synthase activity of the invention, it is possible in step a) to stimulate said cell sample with a lymphocyte activating molecule, such as PMA/ionomycine or anti-CD3 antibody or IL2. Such activation increases CTPS1 (first isoform of CTP synthase) expression in activated lymphocytes, and thus also CTP synthase activity, and may thus be used when one wishes to detect CTPS1 deficiency.

Step b): Preparation of Cell Extract

For preparing the cell extract, cell lysis may be performed by any conventional method well known to one skilled in the art, such as detergent lysis or hypotonic lysis. An example of such preparation is described in examples bellow.

For measuring CTP synthase activity, the sample is preferably collected in a medium preserving proteins and in particular CTP synthase. Preferably, the sample is collected in a neutral to basic intermediate buffer, preferably a buffer of pH between 7 and 9, preferably between 7.5 and 8.5, for instance about 8.

Moreover sodium fluoride (NaF) may be added in order to preserve protein phosphorylation in cell extract.

Step c): Enzymatic Reaction

According to an embodiment, cell extract used in step c) comprises 1 to 10 µg of proteins, preferably 5 to 10 µg and more preferably 8 to 10 µg.

This extract is incubated in very high concentration of UTP, such as 1.3 mM

According to another embodiment of the method for detecting or quantifying CTP synthase activity, in step c) the cell extract is incubated in the presence of, phosphoenolpyruvate (PEP) which may be added to UTP, ATP, GTP and glutamine PEP allows ATP regeneration during the enzymatic reaction, ATP being the main energy source of CTP synthase during enzymatic reaction.

Moreover, at the end of the enzymatic reaction time (linear phase of CTP formation from UTP), the enzymatic reaction is preferably stopped by acidifying the sample to an acidic pH, preferably between 3 and 4 This permits preservation of nucleotide triphosphates, in particular CTP. The complete conversion of UTP to CTP may take about 400 min and the reaction time for measuring CTP synthase activity has been chosen during the linear phase of CTP formation from UTP (1 to 300 min, preferably at 90 min).

Step d): Measurement of CTP Generated from UTP by CTP Synthase Comprised in the Cell Extract In order to detecting and quantifying CTP synthase activity, it is necessary to obtain a good separation of CTP and UTP since their spectral interference is about 16%.

This step is performed using any embodiment described above for the method for detecting or quantifying CTP according to the invention.

Uses of the Methods According to the Invention

The methods of the present invention allow detecting or quantifying CTP and CTP synthase activity very precisely (in particular because they do not lead to protein denaturation), rapidly, easily and inexpensively. Thus, these methods may be used in human medicine in hospital setting, particularly for screening drugs or for adjusting the administered dose of a CTP synthase inhibitor during treatment of a subject, particularly in the field of autoimmune diseases.

CTP and particularly CTP synthase are involved in tumorigenesis and immune deficiency. CTP synthase inhibitors have been already used as anti-cancer compounds and might be used as immunosuppressive treatment (in particular in order to prevent graft rejection) if more specific CTP synthase inhibitors were available. In a third aspect, the present invention thus relates to a method for screening potential immunosuppressive or anti-cancer compounds, said method comprising:
  a) quantifying CTP synthase activity in an untreated cell sample and in a cell sample treated with a test compound using the method of detecting or quantifying CTP synthase activity of the invention,
  b) selecting the test compound as an immunosuppressive or anti-cancer compound if the CTP synthase activity quantified in step a) is lower in the treated cellular sample than in the untreated cellular sample.

The screening method of the invention may be implemented by any appropriate means well known to one skilled in the art.

The method of the invention allows quantifying CTP synthase activity very precisely by using conventional technics for which one skilled in the art has a good command and which are easily implemented at low price and in the hospital conditions. Thus, the method of the invention may be used in pharmacodynamics and in personalized medicine to determine rapidly and precisely the efficiency of CTP synthase activity inhibitors in subjects treated with anti-cancer or immunosuppressive compounds.

Moreover, as mentioned above, said method requires a low quantity of cells for detecting or quantifying CTP synthase activity. Thus, this method is particularly advantageous for use in subjects treated with immunosuppressive compounds who have a low number of lymphocytes in the blood and low CTP synthase activity.

In a forth aspect, the present invention thus relates to a method for determining the appropriate dose of an immunosuppressive or anti-cancer compound inhibiting CTP synthase activity for a treated subject, said method comprising:
  a) quantifying CTP synthase activity using the method for detecting or quantifying CTP synthase activity of the invention in a cell sample from said subject treated with an immunosuppressive or anti-cancer compound,
  b) optimizing the dose of immunosuppressive or anti-cancer compound according to the quantified CTP synthase activity.

In another aspect, the present inventions also relates to a method for treating a subject with an appropriate dose of an immunosuppressive or anti-cancer compound, said method comprising:
  a) administering an immunosuppressive or anti-cancer compound inhibiting CTP synthase activity to the treated subject,
  b) quantifying CTP synthase activity using the method for detecting or quantifying CTP synthase activity of the invention in a cell sample from said subject treated with an immunosuppressive or anti-cancer compound,
  c) optimizing the dose of immunosuppressive or anti-cancer compound, and
  d) administering the optimized dose of immunosuppressive or anti-cancer compound to the treated subject.

According to the present invention the method for detecting or quantifying CTP in a cell sample containing at least two nucleotide triphosphates may thus be used for:
  detecting or quantifying CTP synthase activity;
  screening immunosuppressive or anti-cancer compounds, and/or
  adapting the dose of an immunosuppressive or anti-cancer compound inhibiting CTP synthase activity for a treated subject.

Furthermore, according to the invention, the method for detecting or quantifying CTP synthase activity may be used for:
  screening immunosuppressive or anti-cancer compounds, and/or
  adapting the dose of an immunosuppressive or anti-cancer compound inhibiting CTP synthase activity for a treated subject.

The present invention will be better illustrated in the following examples.

EXAMPLES

Example 1

Materials and Methods

Preparation of Cell Extracts

The cell extracts may be obtained from cultured cells (primary cultures of cells, blasts or cell lines), from blood derived cells. Particularly, mononuclear cells (PBMCs, peripheral blood mononuclear cells) have been isolated from peripheral blood. The cells were washed with phosphate buffer 0.1 M KH2PO4, pH=7.4, and then collected in HEPES buffer 70 mM, pH=8.0, containing 10 mM NaF and protease inhibitors leupeptin and pepstatin to the concentration of 10 μg/mL. The cells were immediately placed in a bath of ethanol and dry ice, and then placed for at least 1 hour at −80° C. The cells were then centrifuged for 30 minutes at 10 000 g at 4° C. The supernatant, containing the cytosolic fraction, was collected and contained proteins were dosed.

Preparation of Reagents

CTP stock solutions and internal standard (stable isotope CTP) were prepared at a concentration of 1 mM and 200 µM, respectively, in Hepes 70 mM and stored at −40° C. CTP calibrators were prepared by dilution of the stock solution in HEPES 70 mM, pH=8.0, containing 12.5 mM $MgCl_2$, 12.5 mM glutamine, 1.25 mM phosphoenolpyruvate, 0.62 mM EDTA and 10 mM NaF to yield a final calibration range of 0.104, 0.416, 1.7, 6.7, 26.6, 106.5 and 426 µM. A 50/50 dilution with $HCLO_4$ 1M was then performed before storage of the calibration curves at −40° C.

Enzymatic Reaction

One to 10 µg of proteins, prepared as described above, were used for measuring CTP synthase activity in a reaction mixture containing 4 µM internal standard, 1.25 mM UTP, 1.25 mM ATP, 0.31 mM GTP, 12.5 mM glutamine, 1.25 mM phosphoenolpyruvate, 0.62 mM EDTA and 10 mM NaF in 15 µL complete HEPES buffer 70 mM, pH=8.0. Enzymatic reaction was carried out at 37° C. for 90 minutes and then, the reaction tubes were cooled on ice and the enzymatic reaction was stopped by adding 15 µL $HCLO_4$ 1 M. The reaction tubes were vortexed and centrifuged for 5 minutes at 12 000 g at 4° C. The supernatants were diluted with the aqueous mobile phase A and transferred to a 384-well plate.

Liquid Chromatography Coupled to Tandem Mass Spectrometry (LC-MS/MS)

Analyses were performed using a Waters chromatographic UPLC system (Acquity™ UPLC) connected to a Waters TQD quadrupole mass spectrometer, operated in the electrospray positive ion mode with selected reaction monitoring (SRM). A 5-µL injection was routinely used, and chromatography was achieved with a. Waters HSS T3, 1.8 µm particle size, 2.1×100 mm column, which was maintained at 30° C. throughout the analysis. The flow rate was 0.5 mL/min. Mobile phase A was 5 mM dibutylamine acetate in water and mobile phase B, 5 mM dibutylamine acetate in acetonitrile. Three distinct mobile-phase gradients were used (see Tables 6a to 6c below).

The detection and quantification of the remaining UTP and formed CTP were carried out using 2 transitions per compound. Spectral conditions selected for the UTP, ATP, GTP, glutamine, CTP and the internal standard are summarized in Tables 4 and 5 below.

TABLE 4

| MS/MS parameters | |
| --- | --- |
| Capillary voltage | 2.90 kV |
| Cone voltage | 50 V |
| Source | 150° C. |
| Desolvatation temperature | 650° C. |
| Cone gas flow | 150 L/hr |
| Desolvatation gas flow | 800 L/hr |
| Collision gas flow | 0.17 mL/min |
| LM1 resolution | 2.8 |
| HM1 resolution | 14.9 |
| Ion energy 1 | 0.2 |
| MS mode entrance | 1 |
| MS mode collision energy | 3 |
| MS mode exit | 1 |

TABLE 4-continued

| MS/MS parameters | |
| --- | --- |
| MS/MS mode entrance | 1 |
| MS/MS mode collision energy | 3 |
| MS/MS mode exit | 1 |
| LM2 resolution | 2.8 |
| HM2 resolution | 14.5 |
| Ion energy 2 | 1.1 |
| Type | MRM |
| Mode ion | ES+ |
| Dwell | 0.004 s |

TABLE 5

| | Transition parameters | | | |
| --- | --- | --- | --- | --- |
| | Quantification transition | Collision energy | Confirmation transition | Collision energy |
| UTP | 482 > 158.9 | 28 | 482 > 384.9 | 20 |
| ATP | 507.9 > 136 | 32 | 507.9 > 507.9 | 2 |
| GTP | 523.9 > 152 | 24 | 523.9 > 523.9 | 2 |
| CTP | 484 > 112 | 20 | 484 > 484 | 2 |
| CTP-EI | 495.8 > 119 | 26 | | |

Results

The obtained results of time gradient are shown on Table 6 below:

HSS T3 with mobile phase at pH=7.0

TABLE 6a

| Chromatography parameters | | | | Nucleotide triphosphates retention times (minutes) | | | |
| --- | --- | --- | --- | --- | --- | --- | --- |
| water + 5 mM DBA | ACN + 5 mM DBA | Flow rate (uL/min) | Duration (min) | UTP | CTP | GTP | ATP |
| 90 | 10 | 500 | 0 | 4.3 | 3.9 | 4.5 | 5.3 |
| 88 | 12 | 500 | 6 | | | | |
| 0 | 100 | 500 | 6.1 | | | | |
| 0 | 100 | 500 | 6.5 | | | | |
| 90 | 10 | 500 | 6.6 | | | | |
| 90 | 10 | 500 | 9 | | | | |

ACN: acetonitrile;
DBA: dibutylamine acetate

HSS T3 with mobile phase at pH=7.0

TABLE 6b

| Chromatography parameters | | | | Nucleotide triphosphates retention times (minutes) | | | |
| --- | --- | --- | --- | --- | --- | --- | --- |
| water + 5 mM DBA | ACN + 5 mM DBA | Flow rate (uL/min) | Duration (min) | UTP | CTP | GTP | ATP |
| 89 | 11 | 500 | 0 | 7.2 | 6.6 | 6.8 | 8.0 |
| 87 | 13 | 500 | 8 | | | | |
| 0 | 100 | 500 | 8.1 | | | | |
| 0 | 100 | 500 | 8.5 | | | | |

TABLE 6b-continued

| Chromatography parameters | | | | Nucleotide triphosphates retention times (minutes) | | | |
|---|---|---|---|---|---|---|---|
| water + 5 mM DBA | ACN + 5 mM DBA | Flow rate (uL/min) | Duration (min) | UTP | CTP | GTP | ATP |
| 89 | 11 | 500 | 8.6 | | | | |
| 89 | 11 | 500 | 12 | | | | |

ACN: acetonitrile;
DBA: dibutylamine acetate

HSS T3 with mobile phase at pH=6.5 (FIG. 1)

TABLE 6c

| Chromatography parameters | | | | Nucleotide triphosphates retention times (minutes) | | | |
|---|---|---|---|---|---|---|---|
| water + 5 mM DBA | ACN + 5 mM DBA | Flow rate (uL/min) | Duration (min) | UTP | CTP | GTP | ATP |
| 89 | 11 | 500 | 0 | 6.5 | 6.0 | 6.4 | 7.5 |
| 87 | 13 | 500 | 8 | | | | |
| 0 | 100 | 500 | 8.1 | | | | |
| 0 | 100 | 500 | 9.1 | | | | |
| 89 | 11 | 500 | 9.2 | | | | |
| 89 | 11 | 500 | 12 | | | | |

ACN: acetonitrile;
DBA: dibutylamine acetate

Specificity of the Tested Method

It was checked if the selected transitions for each molecule of interest were specific to said molecule and if they are not found in cell extracts lacking this said molecule.

Linearity of the Quantifying Method

Figure 2:
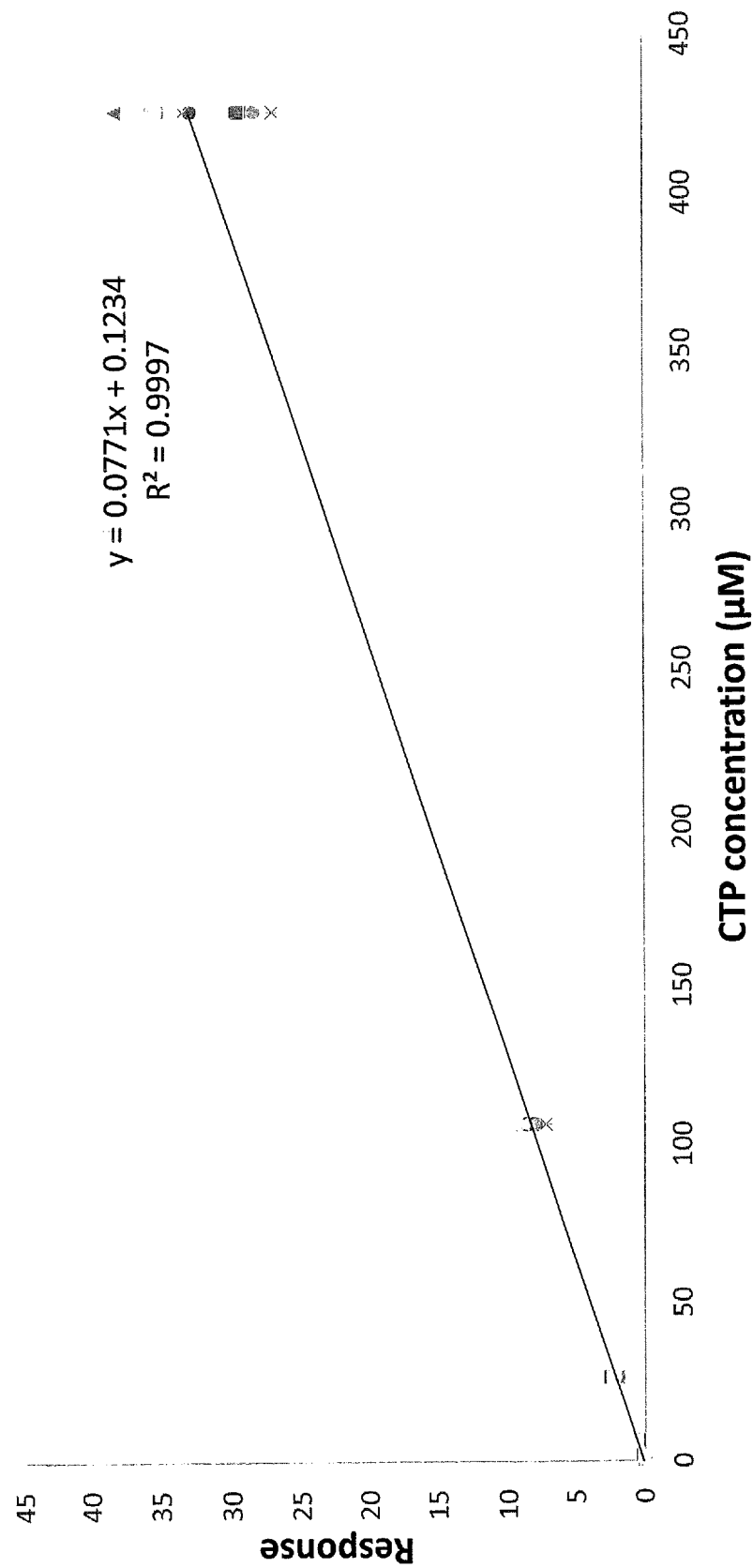
FIG. 2: Calibration curve showing the mean of 11 calibration curves issued after checking linearity and intervariability of 11 independent calibration ranges. The means of these 11 calibration curves is y=0.0771x+1.234 and linear regression coefficient ($r^2$) is $r^2$=0.9997.

The linearity and intervariability of the assay was verified on 11 separate calibrations run over a period of 15 days as shown in FIG. 2. Each individual calibration had an $R^2$ of 0.9966 or greater. The mean regression equation for the 11 calibrations, where regression coefficient are expressed as mean (SD), was as follows: y=[0.0771 (0.0088)]x+[(11234 (0.0809)].

Limit of Detection and Quantification of the Methods of the Invention

The limits of detection and quantification of CTP are respectively 0.635 µM and 2.119 µM.

Intravariability and Intervariability of the Assay Method

1) CTP

To estimate the intravariability and intervariability of CTP assay method, cell extracts were spiked with increasing concentrations of CTP. The intravariability was determined by measuring the samples 10 times the same day, and the intervariability was determined by measuring the samples once a day over a period of 15 days (Table 7).

TABLE 7

Intravariability and Intervariability of the CTP assay method

| Concentration (µM) | Intravariability | | | | Intervariability | | | |
|---|---|---|---|---|---|---|---|---|
| | Mean (µM) | SD | CV (%) | Precision (%) | Mean (µM) | SD | CV (%) | Precision (%) |
| 2 | 2.3 | 0.3 | 10.9 | 92.4 | 2.5 | 0.2 | 9.3 | 98.1 |
| 5 | 4.6 | 0.4 | 7.9 | 92 | 4.8 | 0.5 | 10.3 | 95.5 |
| 10 | 9.3 | 1.1 | 11.6 | 93.5 | 10.7 | 1.4 | 13.4 | 107 |

2) CTP Synthase Activity

In order to estimate the intravariability and intervariability of the CTP synthase activity assay method, the enzyme activity was quantified in isolated cell extracts of resting cells and cells activated by mitogens. Intravariability was determined by measuring the samples 10 times the same day, and the intervariability was determined by measuring the samples once a day over a period of 15 days (Table 8).

TABLE 8

Intravariability and intervariability of CTP synthase activity assay method

| | Intravariability | | | Intervariability | | |
|---|---|---|---|---|---|---|
| | Mean (µM) | SD | CV (%) | Mean (µM) | SD | CV (%) |
| Resting cells | 91.7 | 12 | 13.0 | 92.0 | 20.6 | 22.4 |
| Activated cells | 436 | 25.1 | 5.8 | 547 | 87.4 | 16.0 |

Biological Tests

Kinetics of CTP Synthase Activity

Figure 3:
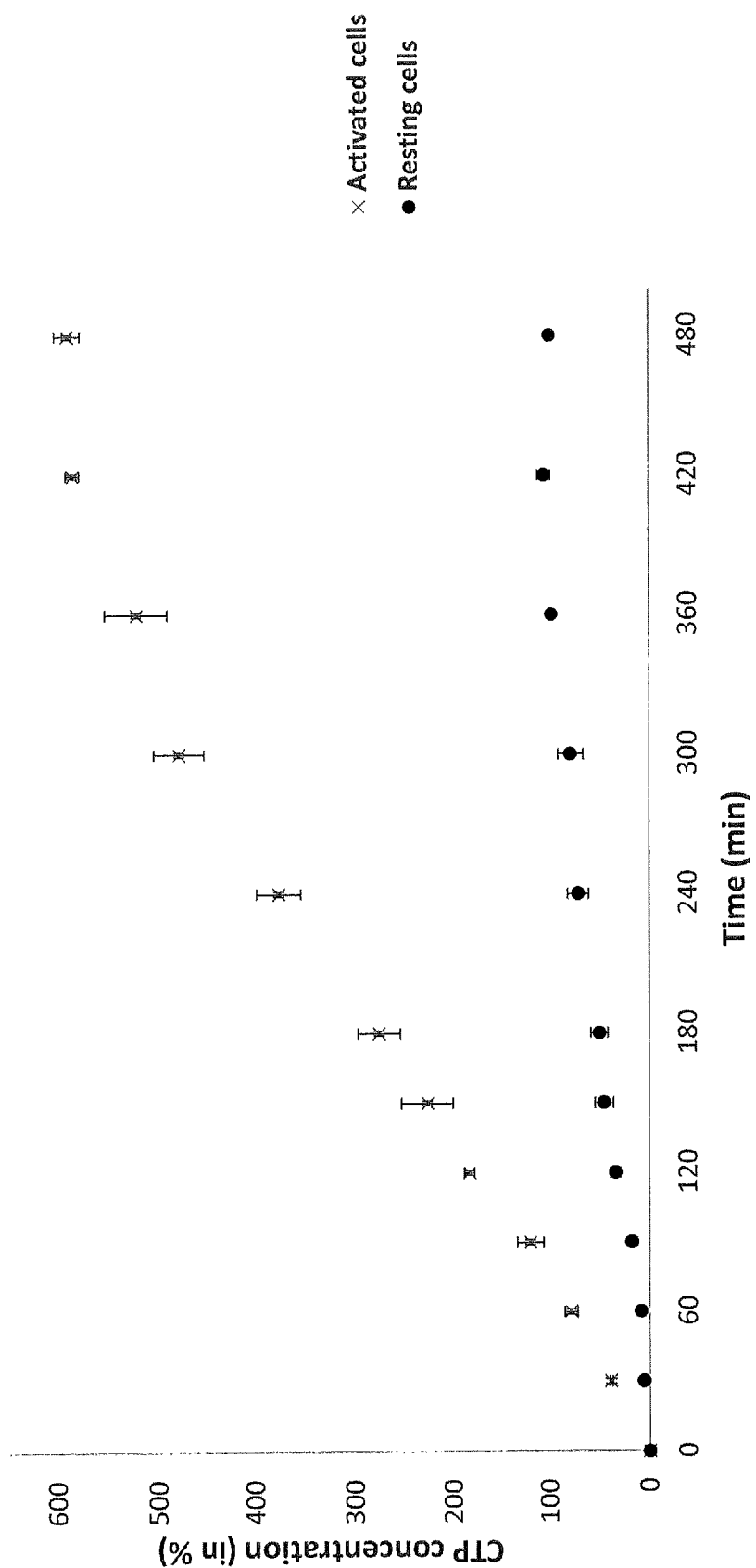
FIG. 3: Kinetics of CTP synthase activity performed by using 10 μg of proteins issued from PBMC cells activated (square) or not (circle) with a mixture of PMA and ionomycine during 48 hours. Enzymatic reaction is liner at first 5 hours of incubation before reaching saturation point.

The kinetics of CTP synthase were assessed on 10 µg of proteins isolated from PBMC, activated or not with a mixture of PMA/ionomycin for 48 hours. The enzymatic reactions were linear during the first 5 hours of incubation before reaching a saturation plateau (FIG. 3). CTP production was significantly higher in cells which have been activated.

Determination of Enzymatic Constants of Michaelis-Menten Km and Vmax

Figure 4:
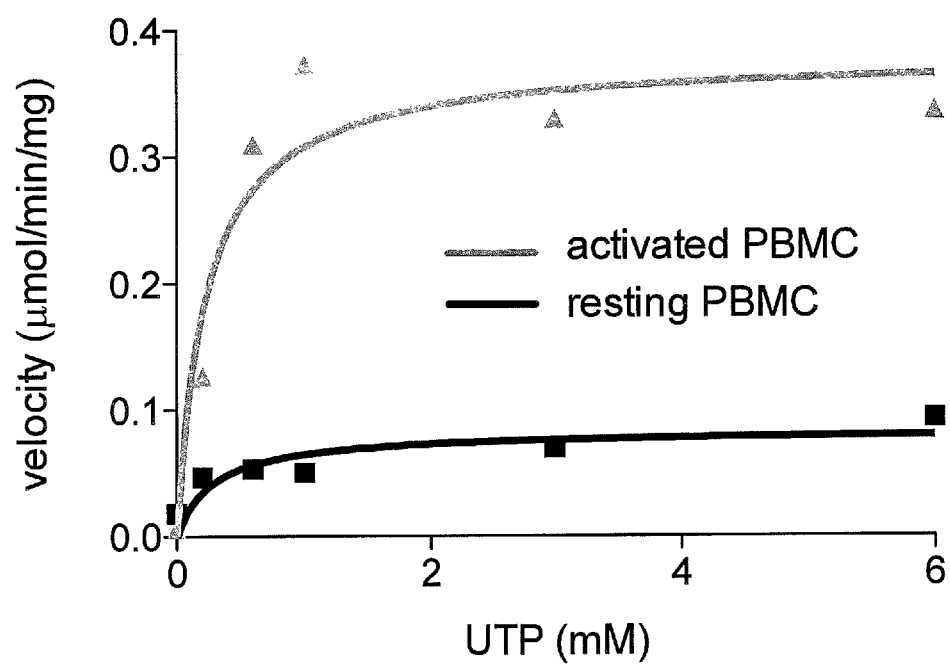
FIG. 4: Determination of CTP synthase kinetic parameters Vmax and Km (Michaelis-Menten enzymatic constants) in activated PBMC (gray line/triangle) and resting PBMC (black line/square) protein extracts. Kinetics of CTP formation were performed during 90 min by using initial concentrations of UTP ranging from 0 to 6 mM. Vmax is increased by a factor of 4.5 in the activated PBMCs compared to resting cells (0.3789±0.091 nmol/min vs 0.083±0.02 nmol/min, respectively) and the Km is not modified by the cell activation (0.2309 and 0.2837 μM, respectively).

Then the enzymatic constants of Michaelis-Menten, Km and Vmax were determined by performing CTP formation kinetics during 90 minutes by using initial concentrations of UTP ranging from 0 to 6 mM. The values obtained for Vmax and Km were of the same order of magnitude as those previously published with radio-isotopic methods (FIG. 4). Vmax was increased by a factor of 4.5 in the PBMCs activated as compared to resting cells (0.3789±0.091 vs 0.083±0.02 mmol/min, respectively) and the Km was not changed by the activation of cells (0.2309 M and 0.2837 M. respectively).

Given the sensitivity and specificity of this new method, it can be used to assess the CTP synthase activity from PBMC sampled from patients without a prior step of proliferation. Thus, the method according to the invention can follow a reduction of CTP synthase activity in patient with homozygous mutation in the gene CTPS1. This assessment can be enhanced by the prior activation of PBMC for example with a mixture of PMA/ionomycin.

Comparative Example 2

Materials and Methods

Other types of chromatography (different columns and mobile phases with or without anionic ion pair reagent) have been tested but they have not allowed accurate separation between the four tested nucleotide triphosphates, and particularly between UTP and CTP.

Particularly, the inventors have tested reversed-phase chromatography, hydrophilic chromatography and ion pairing chromatography.

These assays have been performed in similar conditions than those used in Example 1, except for the type of column used (see Table 9 below), the mobile phase composition and the flow duration.

TABLE 9

Different type of columns (stationary phase) used in the comparative examples

| Columns | Ethylene Bridged Hybrid BEH 300 C18 | High Strength Silica HSS T3 | Charged Surface Hybrid CSH Fluoro-Phenyl | Charged Surface Hybrid CSH Phenyl-Hexyl | Ethylene Bridged Hybrid BEH Amide |
|---|---|---|---|---|---|
| Particles/Size | Ethylene Bridged Hybrid 1.7 μm | High Strength Silica 1.8 μm | Charged Surface Hybrid 3.5 μm | Charged Surface Hybrid 1.7 μm | Ethylene Bridged Hybrid 1.7 μm |
| Grafted with | C18 | T3(C18) | Propyl Fluorophenyl | $C_6$Phenyl | Amide (linker-CONH2) |
| Pores size | 300 Å | 100 Å | 130 Å | 130 Å | 130 Å |
| Type | Reverse phase | Reverse phase | Reverse phase | Reverse phase | Hydrophilic interactions (HILIC) |
| Diameter/Length | 2.1 mm/100 mm | 2.1 mm/100 mm | 2.1 mm/100 mm | 2.1 mm/100 mm | 2.1 mm/100 mm |

In order to prepare the sample for injection, 118 μM of nucleotide triphosphates were mixed with 6 g/L BSA solution and diluted in perchloric acid ($HclO_4$) in ratio 1/6.

The same sample was used for all comparative examples.

The following tests (combination of columns and mobile phases) shown in Table 10 have been performed.

TABLE 10

Different combinations of column and mobile phase for the comparative examples.

| Type of chromatography | Column | Mobile phase |
|---|---|---|
| Reverse phase separation | BEH 300 C18 | water + 0.1% FA and ACN + 0.1% FA |
| | HSS T3 C18 | water + ACN or water + 0.1% FA and ACN + 0.1% FA |
| Hydrophilic interaction | BEH Amide | water + 0.1% FA and ACN + 0.1% FA |
| Anionic ion pairing chromatography | BEH Amide HSS T3 C18 CSH fluorophenyl CSH phenylhexyl | water + 0.5 mM TDHFA and ACN + 0.5 mM TDHFA |

FA: formic acid; ACN: acetonitrile; TDHFA: Perfluoroheptanoic acid.

Results

The time gradients of separation of the 4 nucleotide triphosphates (CTP, UTP, ATP and GTP) and the retention times of the 4 nucleotide triphosphates in such conditions are shown in Tables 11-18 below.

Figure 5:
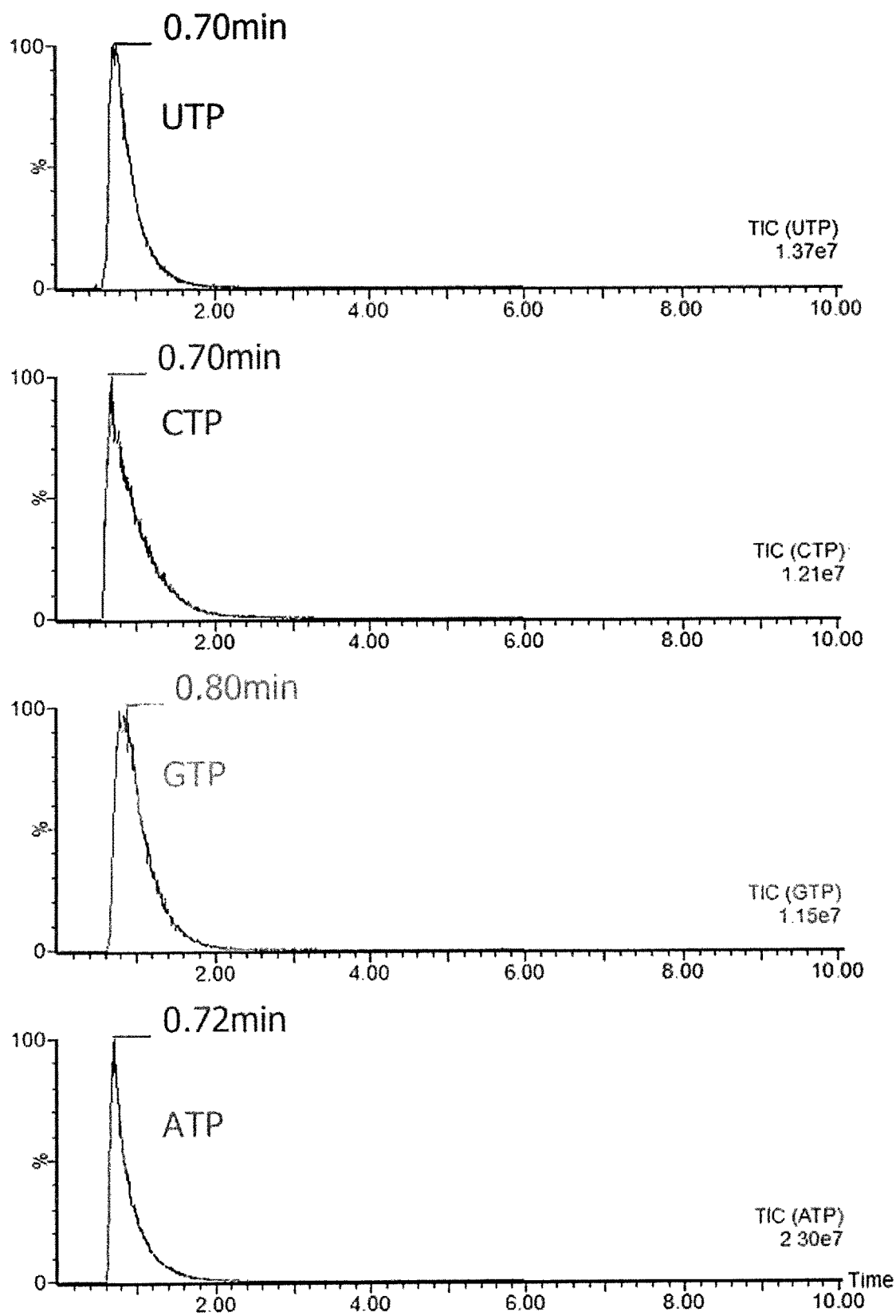
FIG. 5: Linear time gradient of separation (5 min) of four triphosphate nucleotides UTP, CTP, GTP and ATP detected by using BEH 300 C18 column (ACQUITY UPLC BEH300 C18, 1.7 μm, 2.1×100 mm reversed-phase column, Waters) with mobile phase A of 0.1% formic acid (FA) in water and with mobile phase B of 0.1% formic acid in acetonitrile (ACN) without ion pair reagent in the mobile phase (elution with mobile phase=acetonitrile+0.1% formic acid, method used in Martin et al. 2014).
Figure 6:
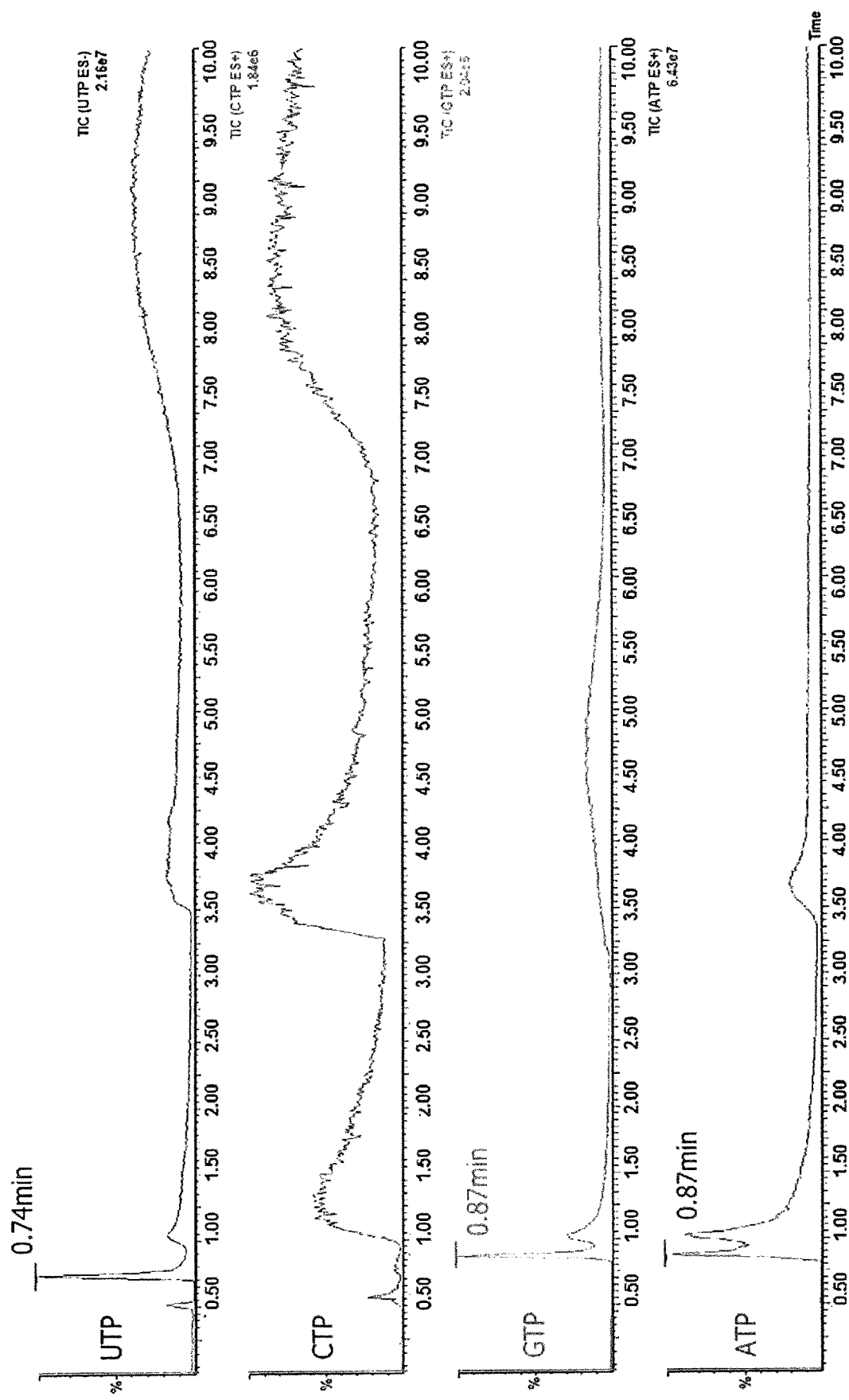
FIG. 6: Linear time gradient of separation (10 min) of four triphosphate nucleotides UTP, CTP, GTP and ATP detected by using HSS T3 column without ion pair reagent in the mobile phase.
Figure 7:
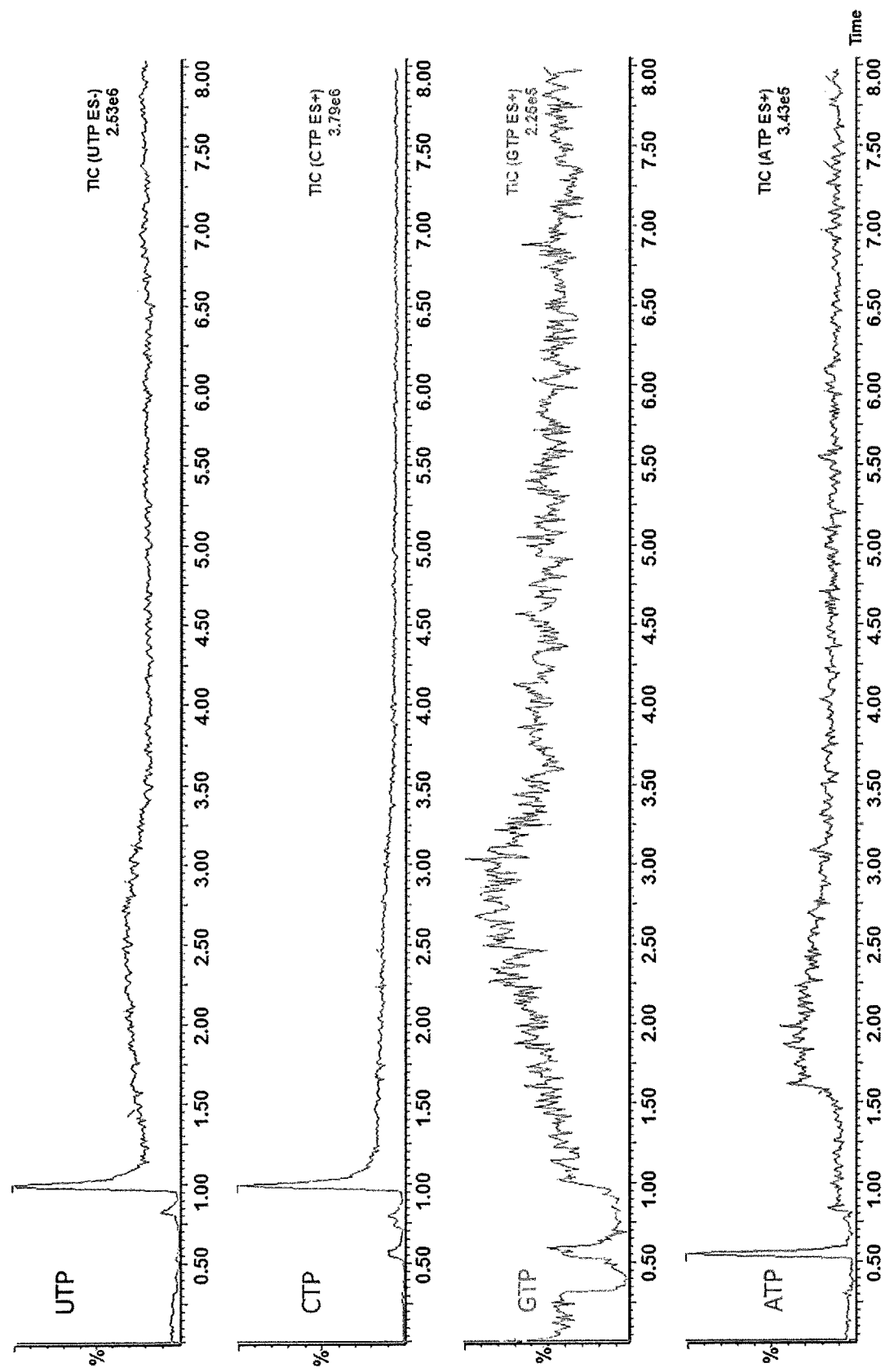
FIG. 7: Linear time gradient of separation (10 min) of four triphosphate nucleotides UTP, CTP, GTP and ATP detected by using HSS T3 column in presence of ACN and perfluoroheptanoic acid (TDHFA which is an anionic ion pair reagent).

1. Reverse phase chromatography without ion-pairing reagents:

BEH 300 C18 (see also FIG. 5)

TABLE 11

| Chromatography parameters | | | | Nucleotide triphosphates retention times (minutes) | | | |
|---|---|---|---|---|---|---|---|
| water + 0.1% FA | ACN + 0.1% FA | Flow rate (uL/min) | Duration (min) | UTP | CTP | GTP | ATP |
| 99 | 1 | 500 | 0 | 0.70 | 0.70 | 0.80 | 0.72 |
| 90 | 10 | 500 | 5 | | | | |
| 1 | 99 | 500 | 5.1 | | | | |
| 1 | 99 | 500 | 6 | | | | |
| 99 | 1 | 500 | 6.1 | | | | |
| 99 | 1 | 500 | 7 | | | | |

ACN: acetonitrile; FA: formic acid.

HSS T3

TABLE 12a

| Chromatography parameters | | | | Nucleotide triphosphates retention times (minutes) | | | |
|---|---|---|---|---|---|---|---|
| water | ACN | Flow rate (uL/min) | Duration (min) | UTP | CTP | GTP | ATP |
| 100 | 0 | 250 | 0 | 1.45 | 1.44 | 1.72 | 1.56 |
| 100 | 0 | 250 | 10 | | | | |
| 0 | 100 | 250 | 10.1 | | | | |
| 0 | 100 | 250 | 12.1 | | | | |
| 100 | 0 | 250 | 13 | | | | |
| 100 | 0 | 250 | 25 | | | | |

ACN: acetonitrile.

HSS T3 (FIG. 6)

TABLE 12b

| Chromatography parameters | | | | Nucleotide triphosphates retention times (minutes) | | | |
|---|---|---|---|---|---|---|---|
| water | ACN | Flow rate (uL/min) | Duration (min) | UTP | CTP | GTP | ATP |
| 100 | 0 | 500 | 0 | 0.74 | ND | 0.87 | 0.87 |
| 0 | 100 | 500 | 10 | | | | |
| 0 | 100 | 500 | 11.1 | | | | |
| 100 | 0 | 500 | 12 | | | | |
| 100 | 0 | 500 | 20 | | | | |

ACN: acetonitrile, ND: not determined

HSS T3

TABLE 13

| Chromatography parameters | | | | Nucleotide triphosphates retention times (minutes) | | | |
|---|---|---|---|---|---|---|---|
| water + 0.1% FA | ACN + 0.1% FA | Flow rate (uL/min) | Duration (min) | UTP | CTP | GTP | ATP |
| 100 | 0 | 250 | 0 | 1.45 | 1.44 | 1.72 | 1.62 |
| 100 | 0 | 250 | 10 | | | | |
| 0 | 100 | 250 | 10.1 | | | | |
| 0 | 100 | 250 | 12.1 | | | | |
| 100 | 0 | 250 | 13 | | | | |
| 100 | 0 | 250 | 25 | | | | |

ACN: acetonitrile; FA: formic acid.

2. Hydrophilic Interaction:
BEH amide

TABLE 14

| water + 0.1% FA | ACN + 0.1% FA | Flow rate (uL/min) | Duration (min) | UTP | CTP | GTP | ATP |
|---|---|---|---|---|---|---|---|
| 2 | 98 | 500 | 0 | 1.49 | 1.49 | 1.47 | 1.48 |
| 2 | 98 | 500 | 5 | | | | |
| 98 | 2 | 500 | 5.1 | | | | |
| 98 | 2 | 500 | 5.8 | | | | |
| 2 | 98 | 500 | 6 | | | | |
| 2 | 98 | 500 | 10 | | | | |

Chromatography parameters / Nucleotide triphosphates retention times (minutes)

ACN: acetonitrile; FA: formic acid.

3. Anionic Ion-Pairing Chromatography:
BEH amide

TABLE 15

| water + 0.5 mM TDHFA | ACN + 0.5 mM TDHFA | Flow rate (uL/min) | Duration (min) | UTP | CTP | GTP | ATP |
|---|---|---|---|---|---|---|---|
| 2 | 98 | 500 | 0 | 0.59 | 0.59 | 0.59 | 0.59 |
| 2 | 98 | 500 | 5 | | | | |
| 98 | 2 | 500 | 5.1 | | | | |
| 98 | 2 | 500 | 5.8 | | | | |
| 2 | 98 | 500 | 6 | | | | |
| 2 | 98 | 500 | 10 | | | | |

ACN: acetonitrile; TDHFA: Perfluoroheptanoic acid.

HSS T3 (FIG. 7)

TABLE 16

| water + 0.5 mM TDHFA | ACN + 0.5 mM TDHFA | Flow rate (uL/min) | Duration (min) | UTP | CTP | GTP | ATP |
|---|---|---|---|---|---|---|---|
| 100 | 0 | 500 | 0 | 1.00 | 0.99 | 0.5 | 0.5 |
| 100 | 0 | 500 | 10 | | | | |
| 0 | 100 | 500 | 10.1 | | | | |
| 0 | 100 | 500 | 10.4 | | | | |
| 100 | 0 | 500 | 11 | | | | |
| 100 | 0 | 500 | 15 | | | | |

ACN: acetonitrile; TDHFA: Perfluoroheptanoic acid.

CSH Fluoro-Phenyl

TABLE 17

| water + 0.5 mM TDHFA | ACN + 0.5 mM TDHFA | Flow rate (uL/min) | Duration (min) | UTP | CTP | GTP | ATP |
|---|---|---|---|---|---|---|---|
| 100 | 0 | 200 | 0 | 1.48 | 1.47 | 1.57 | 1.59 |
| 100 | 0 | 200 | 4 | | | | |
| 0 | 100 | 200 | 4.1 | | | | |
| 0 | 100 | 200 | 6.1 | | | | |
| 100 | 0 | 200 | 7 | | | | |
| 100 | 0 | 200 | 15 | | | | |

ACN: acetonitrile; TDHFA: Perfluoroheptanoic acid.

CSH Phenyl-Hexyl

TABLE 18

| water + 0.5 mM TDHFA | ACN + 0.5 mM TDHFA | Flow rate (uL/min) | Duration (min) | UTP | CTP | GTP | ATP |
|---|---|---|---|---|---|---|---|
| 100 | 0 | 500 | 0 | 0.60 | 0.62 | 0.79 | 0.79 |
| 100 | 0 | 500 | 10 | | | | |
| 0 | 100 | 500 | 11 | | | | |
| 100 | 100 | 500 | 11.1 | | | | |
| 100 | 0 | 500 | 15 | | | | |

ACN: acetonitrile; TDHFA: Perfluoroheptanoic acid.

Spectral Interference

Figure 8:
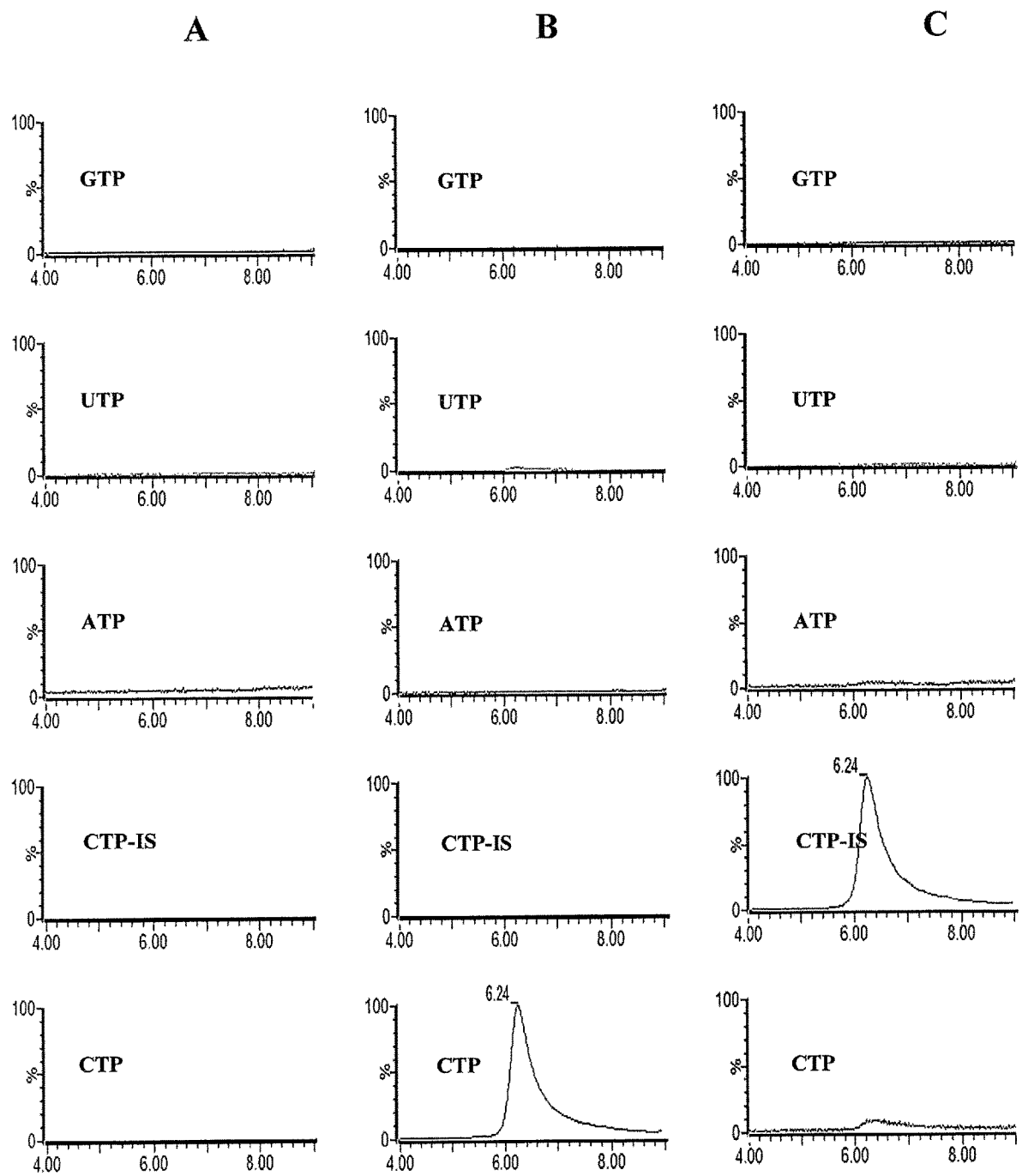
FIG. 8: Spectral interference observed between each compound. Chromatograms obtained for injection of PBMC protein extract with or without (A) known concentration (15 umol/L) of CTP (B), CTP-IS (C), ATP (D), UTP (E) or GTP (F).
Figure 8:
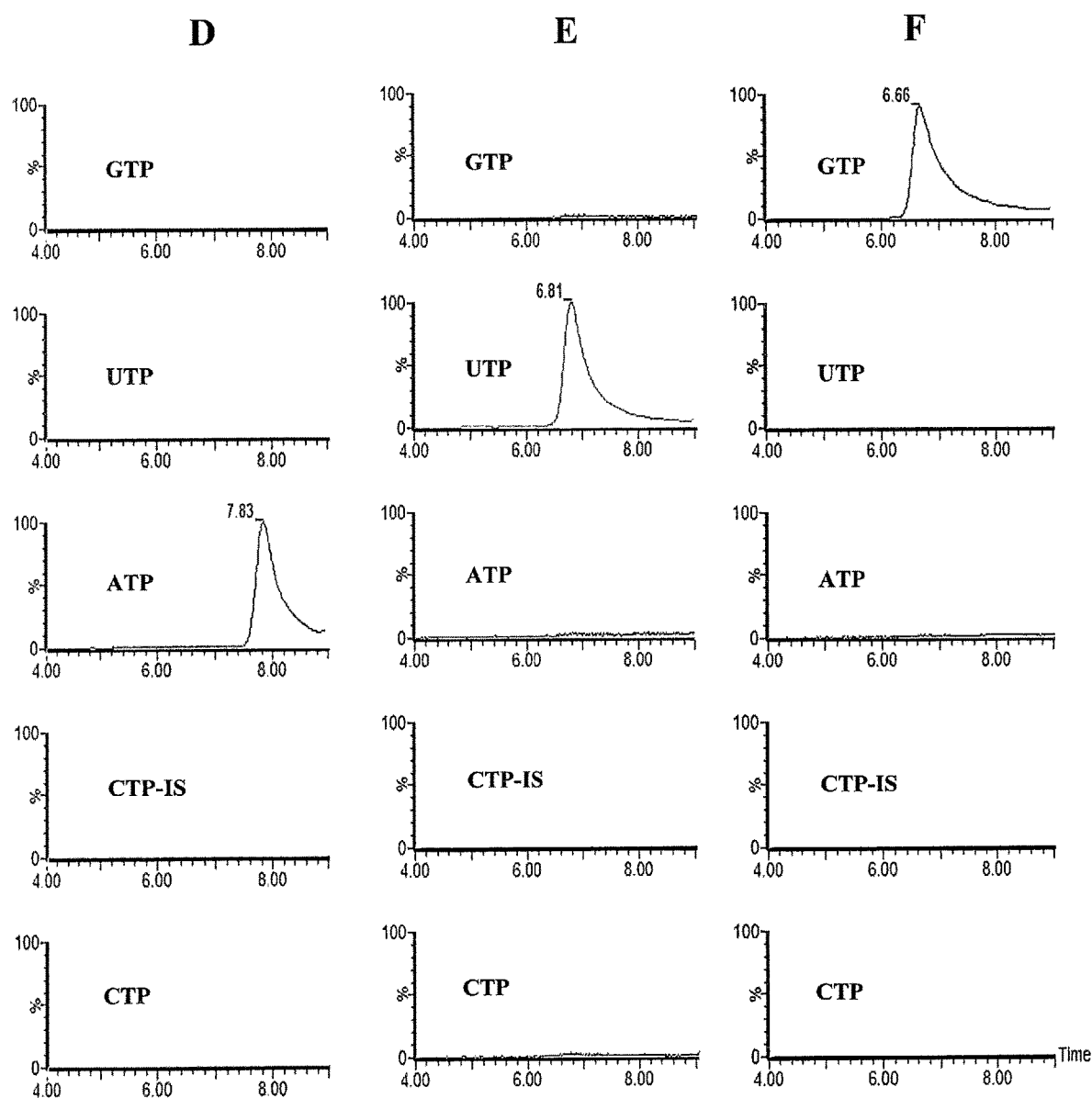

CHROMATOGRAMS OBTAINED FOR INJECTION OF PBMC PROTEIN EXTRACT WITH OR WITHOUT (A) KNOWN CONCENTRATION OF CTP (B), CTP-IS (C), ATP (D), UTP (E) OR GTP (F). 15 □mol/L solutions of each nucleotide involved in the reaction were prepared in 10 µg of PBMC protein extract previously denatured by heat and dialyzed, and were injected separately. This graph presents the chromatograms obtained for each transitions used in the MS/MS analysis (FIG. 8). The contaminating AUC signals were calculated using ratio AUC of nucleotide/AUC of injected nucleotide. Contamination for each compound gave a negligible ratio less than 1%.

BIBLIOGRAPHIC REFERENCES

Brockman R W, Shaddix S C, Williams M, Nelson J A, Rose L M, Schabel F M Jr, The Mechanism of Action of 3-Deazauridine in Tumor Cells Sensitive and Resistant to Arabinosylcytosine, Ann N Y Acad Sci 1975, 255: 501-21.

Cohen S, Megherbi M., Jordheim L. P., Lefebvre I., Perigaud C., Dumontet C., Guitton J., "Simultaneous analysis of eight nucleosides triphosphate in cell lines by liquid chromatography coupled with tandem mass spectrometry", Journal of chromatography B: biomedical sciences & applications, 15 Nov. 2009, 3831-3840.

Cohen S, Jordheim L P, Megherbi M, Dumontet C, Guitton J. Liquid Chromatographic Methods for the Determination of endogenous nucleotides and nucleotide analogs used in cancer therapy: a review, J Chromatogr B Analyt Technol Biomed Life Sci 2010, 878: 1912-28.

Iyengar A and Bearne S L. An Assay for Cytidine 5'-Triphosphate Synthetase Glutaminase Activity Using High Performance Liquid Chromatography, Anal Biochem 2002, 308: 396-400.

Kursula P, Flodin S, Ehn M, Hammarström M, Schiller H, Nordlund P, Stenmark P. Structure of the Synthetase Domain of Human CTP Synthetase, a Target for Anticancer Therapy, Acta Crystallogr Sect F Struct Biol Cryst Commun 2006, 62: 613-17.

Levitzki A and Koshland D E. Role of an Allosteric Effector. Guanosine Triphosphate Activation in Cytosine Triphosphate Synthetase, *Biochemistry* 1972, 11: 241-46.

Long C W and Pardee A B. Cytidine Triphosphate Synthetase of *Escherichia Coli* B. *J Biol Chem* 1967, 242: 4715-21.

Magdenoska O, Martinussen J, Thykaer J, Nielsen K F. Dispersive Solid Phase Extraction Combined with Ion-Pair Ultra High-Performance Liquid Chromatography Tandem Mass Spectrometry for Quantification of Nucleotides in *Lactococcus Lactis*, Anal Biochem 2013, 440: 166-77.

Martin E, Palmic N, Sanquer S, Lenoir C, Hauck F, Mongellaz C, Fabrega S, Nitschke P, Espost M D, Schwartzentruber J, Taylor N, Majewski J, Jabado N, Wynn R F, Picard C, Fischer A, Arkwright P D, Latour S, CTP Synthase 1 Deficiency in Humans Reveals Its Central Role in Lymphocyte Proliferation, Nature 2014, 510: 288-92.

Chen P., Liu Z., Liu S., Xie Z., Aimiuwb J., Pang J., Klisovic R., Blum W., Greyer M. R., Marcucci G., Chan K., A LC-MS/MS method for the analysis of intracellular nucleoside triphosphate levels, Pharmaceutical research, Vol. 26, No:6, June 2009.

Van Kuilenburg A B, Elzinga L, Verschuur A C, Van den Berg A A, Slingerland R J, Van Gennip B. Determination of CTP Synthetase Activity in Crude Cell Homogenates by a Fast and Sensitive Non-Radiochemical Assay Using Anion-Exchange High-Performance Liquid Chromatography, J Chromatogr B, *Biomed Sci and Appl* 1997, 693: 287-95.

Zhao Y, Liu G, Liu Y, Yuan L, Hawthorne D, Shen J X, Guha M, Aubry A. Improved ruggedness of an ion-pairing liquid chromatography/tandem mass spectrometry assay for the quantitative analysis of the triphosphate metabolite of a nucleoside reverse transcriptase inhibitor in peripheral blood mononuclear cells. Rapid Commun Mass Spectrom 2013, 27: 481-8.

WO 2006/107775 A1

The invention claimed is:

1. A method for detecting or quantifying CTP in a sample comprising at least two distinct nucleotide triphosphate, said method comprising:
    a) separating the distinct nucleotide triphosphate by ion-pairing chromatography using a cationic ion pair reagent contained in a mobile phase having a pH comprised between 6 and 7, wherein the sample injected for the chromatography has a pH comprised between 1 and 4 and
    b) detecting or quantifying CTP by mass spectrometry.

2. The method according to claim 1, wherein step a) is performed by using a reverse phase column.

3. The method according to claim 1, wherein the cationic ion pair reagent used in step a) is dibutylamine acetate or tributylamine acetate.

4. The method of claim 1, wherein the concentration of the cationic ion pair reagent in step a) is comprised between 5 and 10 mM.

5. The method of claim 1, wherein a stable isotope CTP standard is added to the sample before step a).

6. The method according to claim 1, wherein the separation in step a) is obtained by forming a binary gradient of an aqueous solution A comprising water and the cationic ion pair reagent and of an organic solution B comprising an organic modifier and the cationic ion pair reagent.

7. The method according to claim 1, wherein the duration of step a) is at most 20 minutes.

8. The method according to claim 1, which total duration is at most 20 minutes.

9. The method according to claim 1, wherein said sample is selected from the group consisting of a blood sample, a tissue sample and a cell sample.

10. A method for detecting or quantifying CTP synthase activity in a cell sample, said method comprising:
    a) optionally, stimulating said cell sample with a lymphocyte activating molecule, such as PMA/ionomycin,
    b) preparing a cell extract by lysing cells of said cell sample,
    c) incubating the cell extract prepared in step b) in the presence of UTP, ATP, GTP and glutamine in conditions suitable for CTP synthase activity; and
    d) detecting or quantifying CTP generated by CTP synthase comprised in the cell extract using the method of claim 1.

11. A method for screening potential immunosuppressive or anti-cancer compounds, said method comprising:
    a) quantifying CTP synthase activity in an untreated cell sample and in a cell sample treated with a test compound using the method of claim 1,
    b) selecting the test compound as an immunosuppressive or anti-cancer compound if the CTP synthase activity quantified in step a) is lower in the treated cellular sample than in the untreated cellular sample.

12. A method for determining the appropriate dose of an immunosuppressive or anti-cancer compound inhibiting CTP synthase activity for a treated subject, said method comprising:
    a) quantifying CTP synthase activity using the method according to claim 1 in a cell sample from said subject treated with an immunosuppressive or anti-cancer compound,
    b) optimizing the dose of immunosuppressive or anti-cancer compound according to the quantified CTP synthase activity.

13. The method according to claim 2, wherein the reverse phase column comprises beads of a diameter inferior or equal to 10 µm grafted with a hydrophobic molecule.

14. The method of claim 4, wherein the concentration of the cationic ion pair reagent in step a) is comprised between 5 and 8 mM or between 5 and 6 mM.

15. The method according to claim 6, wherein the binary gradient is a quasi-isocratic gradient, in which an increase of the % (v/v) of the organic solution B is at most 10% (v/v), at most 5% (v/v) or at most 2% (v/v) from the beginning (t=0) to the end of the separation step a).

16. The method according to claim 9, wherein said sample is a PBMC sample or a lymphocyte sample.

17. The method according to claim 16, wherein the column is a High Strength Silica (HSS) column.

18. The method according to claim 1, wherein:
    (i) step a) is performed by using a reverse phase column comprising beads of a diameter inferior or equal to 10 µm grafted with a hydrophobic molecule;
    (ii) the cationic ion pair reagent used in step a) is dibutylamine acetate or tributylamine acetate, comprised at concentration between 5 and 10 mM,
    (iii) the separation in step a) is obtained by forming a binary gradient of an aqueous solution A comprising water and the cationic ion pair reagent and of an organic solution B comprising an organic modifier and the cationic ion pair reagent, and
    (iv) the sample is a blood sample, a tissue sample and a cell sample.

19. The method according to claim 1, wherein:
(i) step a) is performed by using a High Strength Silica (HSS) column;
(ii) the cationic ion pair reagent used in step a) is dibutylamine acetate or tributylamine acetate, comprised at concentration between 5 and 8 mM,
(iii) the separation in step a) is obtained by forming a binary gradient of an aqueous solution A comprising water and the cationic ion pair reagent and of an organic solution B comprising an organic modifier and the cationic ion pair reagent, wherein the binary gradient is a quasi-isocratic gradient, in which an increase of the % (v/v) of the organic solution B is at most 10% (v/v), and
(iv) the sample is a PBMC sample or a lymphocyte sample.

\* \* \* \* \*